United States Patent
Kondo et al.

(10) Patent No.: US 9,751,917 B2
(45) Date of Patent: Sep. 5, 2017

(54) POLYNUCLEOTIDE FOR CELL SURFACE LAYER EXPRESSION

(71) Applicant: National University Corporation Kobe University, Hyogo (JP)

(72) Inventors: Akihiko Kondo, Hyogo (JP); Tomohisa Hasunuma, Hyogo (JP); Kentaro Inokuma, Hyogo (JP)

(73) Assignee: National University Corporation Kobe University, Hyogo (JP)

( * ) Notice: Subject to any disclaimer, the term of this patent is extended or adjusted under 35 U.S.C. 154(b) by 0 days.

(21) Appl. No.: 14/778,250

(22) PCT Filed: Mar. 25, 2014

(86) PCT No.: PCT/JP2014/058189
§ 371 (c)(1),
(2) Date: Sep. 18, 2015

(87) PCT Pub. No.: WO2014/157141
PCT Pub. Date: Oct. 2, 2014

(65) Prior Publication Data
US 2016/0326224 A1    Nov. 10, 2016

(30) Foreign Application Priority Data
Mar. 25, 2013  (JP) ................ 2013-062795

(51) Int. Cl.
C12N 1/14     (2006.01)
C07K 14/39    (2006.01)
C12P 7/10     (2006.01)
C12N 9/42     (2006.01)

(52) U.S. Cl.
CPC .......... C07K 14/39 (2013.01); C12N 9/2437 (2013.01); C12P 7/10 (2013.01); C12Y 302/01004 (2013.01); C07K 2319/035 (2013.01); Y02E 50/16 (2013.01); Y02E 50/17 (2013.01)

(58) Field of Classification Search
CPC .. C12N 15/81; C07K 14/39; C07K 2319/035; C12Y 302/01004
USPC .................................................... 435/255.2
See application file for complete search history.

(56) References Cited

FOREIGN PATENT DOCUMENTS

| JP | 2005245335 A | 9/2005 |
|---|---|---|
| JP | 2007189909 A | 8/2007 |
| JP | 2008086310 A | 4/2008 |
| JP | 2011030563 A | 2/2011 |
| JP | 2011160727 A | 8/2011 |
| JP | 2011167096 A | 9/2011 |
| JP | 2012139211 A | 7/2012 |

OTHER PUBLICATIONS

International Preliminary Report on Patentability issued in corresponding International Patent Application No. PCT/JP2014/058189 dated Dec. 3, 2015 (8 pages).
I. Hagen et al., "Sed1p and Srl1p are required to compensate for cell wall instability in Saccharomyces cerevisiae mutants defective in multiple GPI-anchored mannoproteins", Molecular Microbiology, vol. 52, 2004, pp. 1413-1425.
Van Der Vaart et al., "Comparison of Cell Wall Proteins of Saccharomyces cerevisiae as Anchors for Cell Surface Expression of Heterologous Proteins", Applied and Environmental Microbiology, vol. 63, 1997 pp. 615-620.
Liu et al., "Surface display of active lipase in Saccharomyces cerevisiae using Cwp2 as an anchor protein", Biotechnol Lett, vol. 32, 2010, pp. 255-260.
Skrzypek et al., "Suppressor Gene Analysis Reveals an Essential Role for Sphingolipids in Transport of Glycosylphosphatidylinositol-Anchored Proteins in Saccharomyces cerevisiae", Journal of Bacteriology, vol. 179, 1997, pp. 1513-1520.
Gibson et al., "Enzymatic assembly of DNA molecules up to several hundred kilobases", Nature Methods, vol. 6, 2009, pp. 343-345.
C. B. Brachmann et al., "Designer Deletion Strains derived from Saccharomyces cerevisiae S288C: a Useful set of Strains and Plasmids for PCR-mediated Gene Disruption and Other Applications", Yeast, 1998, vol. 14, pp. 115-132.
Katahira et al., "Ethanol fermentation from lignocellulosic hydrolysate by a recombinant xylose- and cellooligosaccharide-assimilating yeast strain", Appl Microbiol Biotechnol, 2006, vol. 72, pp. 1136-1143.
Yamada et al., "Novel strategy for yeast construction using delta-integration and cell fusion to efficiently produce ethanol from raw starch", Appl Microbiol Biotechnol, vol. 85, 2010, pp. 1491-1498.
Yamakawa et al., "Repeated fermentation from raw starch using Saccharomyces cerevisiae displaying both glucoamylase and alpha-amylase", Enzyme and Microbial Technology, 2012, vol. 50, pp. 343-347.
International Search Report issued in corresponding International Patent Application No. PCT/JP2014/058189 dated Jul. 1, 2014 (2 pages).
Inokuma et al., "Efficient yeast cell-surface display of exo- and endo-cellulase using the SED1 anchoring region and its original promoter," Biotechnology for Biofuels, vol. 7, No. 8, 2014, pp. 1-11.
Kotaka et al., "Enhancement of β-glucosidase activity on the cell-surface of sake yeast by disruption of SED1," Journal of Bioscience and Bioengineering, vol. 109, No. 5, 2010, pp. 442-446.
Ram et al., "Green fluorescent protein-cell wall fusion proteins are covalently incorporated into the cell wall of Saccharomyces cerevisiae," FEMS Microbiology Letters, vol. 162, 1998, pp. 249-255.
Su et al., "Surface display of active lipase in Pichia pastoris using Sed1 as an anchor protein," Biotechnology Letters, vol. 32, 2010, pp. 1131-1136.

(Continued)

Primary Examiner — Tekchand Saidha
(74) Attorney, Agent, or Firm — Kilyk & Bowersox, P.L.L.C.

(57) ABSTRACT

Disclosed is a polynucleotide for cell surface expression. The polynucleotide of the invention comprises a promoter, a secretion signal sequence, a sequence encoding an intended protein, and a sequence encoding a cell surface-localized protein or a cell membrane-binding domain thereof, wherein the promoter is a promoter of a gene encoding the cell surface-localized protein. Provided is a polynucleotide for cell surface expression allowing the production of yeast displaying an enzyme on the cell surface with a high activity.

11 Claims, 6 Drawing Sheets

(56) References Cited

OTHER PUBLICATIONS

Wheeler et al., "A *Saccharomyces cerevisiae* mutant with increased virulence", PNAS, vol. 100, No. 5, 2003, pp. 2766-2770.

SEQUENCE LISTING

<160> NUMBER OF SEQ ID NOS: 49

<210> SEQ ID NO 1
<211> LENGTH: 1017

```
<212> TYPE: DNA
<213> ORGANISM: Saccharomyces cerevisiae
<220> FEATURE:
<221> NAME/KEY: CDS
<222> LOCATION: (1)..(1017)
<223> OTHER INFORMATION: Sed1

<400> SEQUENCE: 1
```

| | | | | | | | | | | | | | | | | |
|---|---|---|---|---|---|---|---|---|---|---|---|---|---|---|---|---|
| atg | aaa | tta | tca | act | gtc | cta | tta | tct | gcc | ggt | tta | gcc | tcg | act | act | 48 |
| Met | Lys | Leu | Ser | Thr | Val | Leu | Leu | Ser | Ala | Gly | Leu | Ala | Ser | Thr | Thr | |
| 1 | | | | 5 | | | | | 10 | | | | | 15 | | |
| ttg | gcc | caa | ttt | tcc | aac | agt | aca | tct | gct | tct | tcc | acc | gat | gtc | act | 96 |
| Leu | Ala | Gln | Phe | Ser | Asn | Ser | Thr | Ser | Ala | Ser | Ser | Thr | Asp | Val | Thr | |
| | | | 20 | | | | | 25 | | | | | 30 | | | |
| tcc | tcc | tct | tcc | atc | tcc | act | tcc | tct | ggc | tca | gta | act | atc | aca | tct | 144 |
| Ser | Ser | Ser | Ser | Ile | Ser | Thr | Ser | Ser | Gly | Ser | Val | Thr | Ile | Thr | Ser | |
| | | 35 | | | | | 40 | | | | | 45 | | | | |
| tct | gaa | gct | cca | gaa | tcc | gac | aac | ggt | acc | agc | aca | gct | gca | cca | act | 192 |
| Ser | Glu | Ala | Pro | Glu | Ser | Asp | Asn | Gly | Thr | Ser | Thr | Ala | Ala | Pro | Thr | |
| 50 | | | | | 55 | | | | | 60 | | | | | | |
| gaa | acc | tca | aca | gag | gct | cca | acc | act | gct | atc | cca | act | aac | ggt | acc | 240 |
| Glu | Thr | Ser | Thr | Glu | Ala | Pro | Thr | Thr | Ala | Ile | Pro | Thr | Asn | Gly | Thr | |
| 65 | | | | | 70 | | | | | 75 | | | | | 80 | |
| tct | act | gaa | gct | cca | acc | act | gct | atc | cca | act | aac | ggt | acc | tct | act | 288 |
| Ser | Thr | Glu | Ala | Pro | Thr | Thr | Ala | Ile | Pro | Thr | Asn | Gly | Thr | Ser | Thr | |
| | | | | 85 | | | | | 90 | | | | | 95 | | |
| gaa | gct | cca | act | gat | act | act | act | gaa | gct | cca | acc | acc | gct | ctt | cca | 336 |
| Glu | Ala | Pro | Thr | Asp | Thr | Thr | Thr | Glu | Ala | Pro | Thr | Thr | Ala | Leu | Pro | |
| | | | 100 | | | | | 105 | | | | | 110 | | | |
| act | aac | ggt | act | tct | act | gaa | gct | cca | act | gat | act | act | act | gaa | gct | 384 |
| Thr | Asn | Gly | Thr | Ser | Thr | Glu | Ala | Pro | Thr | Asp | Thr | Thr | Thr | Glu | Ala | |
| | | 115 | | | | | 120 | | | | | 125 | | | | |
| cca | acc | acc | ggt | ctt | cca | acc | aac | ggt | acc | act | tca | gct | ttc | cca | cca | 432 |
| Pro | Thr | Thr | Gly | Leu | Pro | Thr | Asn | Gly | Thr | Thr | Ser | Ala | Phe | Pro | Pro | |
| 130 | | | | | 135 | | | | | 140 | | | | | | |
| act | aca | tct | ttg | cca | cca | agc | aac | act | acc | acc | act | cct | cct | tac | aac | 480 |
| Thr | Thr | Ser | Leu | Pro | Pro | Ser | Asn | Thr | Thr | Thr | Thr | Pro | Pro | Tyr | Asn | |
| 145 | | | | | 150 | | | | | 155 | | | | | 160 | |
| cca | tct | act | gac | tac | acc | act | gac | tac | act | gta | gtc | act | gaa | tat | act | 528 |
| Pro | Ser | Thr | Asp | Tyr | Thr | Thr | Asp | Tyr | Thr | Val | Val | Thr | Glu | Tyr | Thr | |
| | | | | 165 | | | | | 170 | | | | | 175 | | |
| act | tac | tgt | cca | gaa | cca | acc | act | ttc | acc | aca | aac | ggt | aag | act | tac | 576 |
| Thr | Tyr | Cys | Pro | Glu | Pro | Thr | Thr | Phe | Thr | Thr | Asn | Gly | Lys | Thr | Tyr | |
| | | | 180 | | | | | 185 | | | | | 190 | | | |
| acc | gtc | act | gaa | cca | acc | aca | ttg | act | atc | act | gac | tgt | cca | tgc | acc | 624 |
| Thr | Val | Thr | Glu | Pro | Thr | Thr | Leu | Thr | Ile | Thr | Asp | Cys | Pro | Cys | Thr | |
| | | 195 | | | | | 200 | | | | | 205 | | | | |
| att | gaa | aag | cca | aca | acc | aca | tca | acc | acc | gaa | tac | act | gta | gtc | act | 672 |
| Ile | Glu | Lys | Pro | Thr | Thr | Thr | Ser | Thr | Thr | Glu | Tyr | Thr | Val | Val | Thr | |
| 210 | | | | | 215 | | | | | 220 | | | | | | |
| gag | tac | act | act | tac | tgt | cca | gaa | cca | acc | act | ttc | acc | aca | aac | ggt | 720 |
| Glu | Tyr | Thr | Thr | Tyr | Cys | Pro | Glu | Pro | Thr | Thr | Phe | Thr | Thr | Asn | Gly | |
| 225 | | | | 230 | | | | | 235 | | | | | 240 | | |
| aag | act | tac | acc | gtc | act | gaa | cca | acc | act | ttg | act | atc | act | gac | tgt | 768 |
| Lys | Thr | Tyr | Thr | Val | Thr | Glu | Pro | Thr | Thr | Leu | Thr | Ile | Thr | Asp | Cys | |
| | | | 245 | | | | | 250 | | | | | 255 | | | |
| cca | tgt | act | att | gaa | aag | agc | gaa | gcc | cct | gag | tct | tct | gtc | cca | gtt | 816 |
| Pro | Cys | Thr | Ile | Glu | Lys | Ser | Glu | Ala | Pro | Glu | Ser | Ser | Val | Pro | Val | |
| | | 260 | | | | | 265 | | | | | 270 | | | | |
| acc | gaa | tct | aag | ggc | act | acc | acc | aaa | gaa | aca | ggt | gtt | act | acc | aaa | 864 |
| Thr | Glu | Ser | Lys | Gly | Thr | Thr | Thr | Lys | Glu | Thr | Gly | Val | Thr | Thr | Lys | |

```
                     275                 280                 285
caa acc aca gcc aac cca agt cta acc gtc tcc aca gtc gtc cca gtt       912
Gln Thr Thr Ala Asn Pro Ser Leu Thr Val Ser Thr Val Val Pro Val
    290                 295                 300 tca tcc tct gct tct tct cat tcc gtt gtc atc aac agt aac ggt gct       960
Ser Ser Ser Ala Ser Ser His Ser Val Val Ile Asn Ser Asn Gly Ala
305                 310                 315                 320 aac gtc gtc gtt cca ggt gct tta ggt ttg gct ggt gtt gct atg tta      1008
Asn Val Val Val Pro Gly Ala Leu Gly Leu Ala Gly Val Ala Met Leu
                325                 330                 335 ttc tta taa                                                          1017
Phe Leu <210> SEQ ID NO 2
<211> LENGTH: 338
<212> TYPE: PRT
<213> ORGANISM: Saccharomyces cerevisiae

<400> SEQUENCE: 2

Met Lys Leu Ser Thr Val Leu Leu Ser Ala Gly Leu Ala Ser Thr Thr
1               5                   10                  15

Leu Ala Gln Phe Ser Asn Ser Thr Ser Ala Ser Ser Thr Asp Val Thr
            20                  25                  30

Ser Ser Ser Ser Ile Ser Thr Ser Ser Gly Ser Val Thr Ile Thr Ser
        35                  40                  45

Ser Glu Ala Pro Glu Ser Asp Asn Gly Thr Ser Thr Ala Ala Pro Thr
    50                  55                  60

Glu Thr Ser Thr Glu Ala Pro Thr Thr Ala Ile Pro Thr Asn Gly Thr
65                  70                  75                  80

Ser Thr Glu Ala Pro Thr Thr Ala Ile Pro Thr Asn Gly Thr Ser Thr
                85                  90                  95

Glu Ala Pro Thr Asp Thr Thr Glu Ala Pro Thr Thr Ala Leu Pro
            100                 105                 110

Thr Asn Gly Thr Ser Thr Glu Ala Pro Thr Asp Thr Thr Glu Ala
            115                 120                 125

Pro Thr Thr Gly Leu Pro Thr Asn Gly Thr Thr Ser Ala Phe Pro Pro
    130                 135                 140

Thr Thr Ser Leu Pro Pro Ser Asn Thr Thr Thr Pro Pro Tyr Asn
145                 150                 155                 160

Pro Ser Thr Asp Tyr Thr Thr Asp Tyr Thr Val Val Thr Glu Tyr Thr
                165                 170                 175

Thr Tyr Cys Pro Glu Pro Thr Thr Phe Thr Thr Asn Gly Lys Thr Tyr
            180                 185                 190

Thr Val Thr Glu Pro Thr Thr Leu Thr Ile Thr Asp Cys Pro Cys Thr
            195                 200                 205

Ile Glu Lys Pro Thr Thr Thr Ser Thr Glu Tyr Thr Val Val Thr
    210                 215                 220

Glu Tyr Thr Thr Tyr Cys Pro Glu Pro Thr Thr Phe Thr Thr Asn Gly
225                 230                 235                 240

Lys Thr Tyr Thr Val Thr Glu Pro Thr Thr Leu Thr Ile Thr Asp Cys
                245                 250                 255

Pro Cys Thr Ile Glu Lys Ser Glu Ala Pro Glu Ser Ser Val Pro Val
            260                 265                 270

Thr Glu Ser Lys Gly Thr Thr Thr Lys Glu Thr Gly Val Thr Thr Lys
        275                 280                 285
```

```
Gln Thr Thr Ala Asn Pro Ser Leu Thr Val Ser Thr Val Val Pro Val
        290                 295                 300

Ser Ser Ser Ala Ser Ser His Ser Val Val Ile Asn Ser Asn Gly Ala
305                 310                 315                 320

Asn Val Val Val Pro Gly Ala Leu Gly Leu Ala Gly Val Ala Met Leu
                325                 330                 335

Phe Leu

<210> SEQ ID NO 3
<211> LENGTH: 279
<212> TYPE: DNA
<213> ORGANISM: Saccharomyces cerevisiae
<220> FEATURE:
<221> NAME/KEY: CDS
<222> LOCATION: (1)..(279)
<223> OTHER INFORMATION: Cwp2

<400> SEQUENCE: 3 atg caa ttc tct act gtc gct tcc gtt gct ttc gtc gct ttg gct aac    48
Met Gln Phe Ser Thr Val Ala Ser Val Ala Phe Val Ala Leu Ala Asn
1               5                   10                  15 ttt gtt gcc gct gaa tcc gct gcc gcc att tct caa atc act gac ggt    96
Phe Val Ala Ala Glu Ser Ala Ala Ala Ile Ser Gln Ile Thr Asp Gly
                20                  25                  30 caa atc caa gct act acc act gct acc acc gaa gct acc acc act gct   144
Gln Ile Gln Ala Thr Thr Thr Ala Thr Thr Glu Ala Thr Thr Thr Ala
            35                  40                  45 gcc cca tct tcc acc gtt gaa act gtt tct cca tcc agc acc gaa act   192
Ala Pro Ser Ser Thr Val Glu Thr Val Ser Pro Ser Ser Thr Glu Thr
        50                  55                  60 atc tct caa caa act gaa aat ggt gct gct aag gcc gct gtc ggt atg   240
Ile Ser Gln Gln Thr Glu Asn Gly Ala Ala Lys Ala Ala Val Gly Met
65                  70                  75                  80 ggt gcc ggt gct cta gct gct gct gct atg ttg tta taa               279
Gly Ala Gly Ala Leu Ala Ala Ala Ala Met Leu Leu
                85                  90

<210> SEQ ID NO 4
<211> LENGTH: 92
<212> TYPE: PRT
<213> ORGANISM: Saccharomyces cerevisiae

<400> SEQUENCE: 4

Met Gln Phe Ser Thr Val Ala Ser Val Ala Phe Val Ala Leu Ala Asn
1               5                   10                  15

Phe Val Ala Ala Glu Ser Ala Ala Ala Ile Ser Gln Ile Thr Asp Gly
                20                  25                  30

Gln Ile Gln Ala Thr Thr Thr Ala Thr Thr Glu Ala Thr Thr Thr Ala
            35                  40                  45

Ala Pro Ser Ser Thr Val Glu Thr Val Ser Pro Ser Ser Thr Glu Thr
        50                  55                  60

Ile Ser Gln Gln Thr Glu Asn Gly Ala Ala Lys Ala Ala Val Gly Met
65                  70                  75                  80

Gly Ala Gly Ala Leu Ala Ala Ala Ala Met Leu Leu
                85                  90

<210> SEQ ID NO 5
<211> LENGTH: 800
<212> TYPE: DNA
<213> ORGANISM: Saccharomyces cerevisiae
<220> FEATURE:
```

```
<221> NAME/KEY: misc_feature
<222> LOCATION: (1)..(800)
<223> OTHER INFORMATION: Sed1 promoter

<400> SEQUENCE: 5
attggatata gaaaattaac gtaaggcagt atcttttcac aatgtacttg caacgcggcg      60
acttaaagtt gaagtacaac ctgcagcagc ggcttttttgt acggtacgcc aaactgtcaa    120
tggataatat tgcgtagacc gaaaaaggta atcctcaaca ctacccgtgg tggatgacct    180
aaagcagtaa tattggttgg aattatctcc cagacggcac cgtctccccg agaaagctta    240
gccccgaggt ctaccttcca tacaccactg attgctccac gtcatgcggc cttctttcga    300
ggacaaaaag gcatatatcg ctaaaattag ccatcagaac cgttattgtt attatatttt    360
cattacgaaa gaggagaggg cccagcgcgc cagagcacac acggtcattg attactttat    420
ttggctaaag atccatccct tctcgatgtc atctctttcc attcttgtgt attttttgatt   480 gaaaatgatt ttttgtccac taatttctaa aaataagaca aaaagccttt aagcagtttt    540
tcatccattt tactacggta aaatgaatta gtacggtatg gctcccagtc gcattatttt     600
tagattggcc gtaggggctg ggtagaact agagtaagga acattgctct gccctctttt      660
gaactgtcat ataaataccct gacctatttt attctccatt atcgtattat ctcacctctc    720
tttttctatt ctcttgtaat tattgattta tagtcgtaac tacaaagaca agcaaaataa    780
aatacgttcg ctctattaag                                                800

<210> SEQ ID NO 6
<211> LENGTH: 516
<212> TYPE: DNA
<213> ORGANISM: Saccharomyces cerevisiae
<220> FEATURE:
<221> NAME/KEY: misc_feature
<222> LOCATION: (1)..(516)
<223> OTHER INFORMATION: Cwp2 promoter

<400> SEQUENCE: 6
cgaactgaac tgccttagct ccgaagggca attccacagg cactccgcgg ggcccggcca    60
aggcccaaaa ggcgtggaat atgcgcgttt tggggccata acaccagta ccacggccgg     120 aacgggccat ataataagtt tttcactctc aagaatggta aacgtaaata ggaacatccc    180
actaccctag aaattgcgga aatttcgcgc ttatcattag aaaatctgga accgtccttt    240
ttcctctttc ttgcatttcc cttccgtat tattgccatt ctttaactgc atttggggaa    300
ccgtagacca aaagccaaac agagaaatgt aacgttctaa aaaaaaaaca acgaaaaaat    360
tgaaaaataa gatacaataa tcgtatataa atcaggcttc ttgttcatca ttttcaattc    420
tcttcttgcc atcccttttc ctatctttgt tcttttcttc tcataatcaa gaataaataa    480
cttcatcaca ttcgctacac actaacaaga aaaaaa                              516

<210> SEQ ID NO 7
<211> LENGTH: 39
<212> TYPE: DNA
<213> ORGANISM: Artificial Sequence
<220> FEATURE:
<223> OTHER INFORMATION: SED1a-XhoI-F primer, which is synthesized and a
      DNA sequence

<400> SEQUENCE: 7
gccatcctcg agtaaattat caactgtcct attatctgc                            39

<210> SEQ ID NO 8
```

-continued

```
<211> LENGTH: 38
<212> TYPE: DNA
<213> ORGANISM: Artificial Sequence
<220> FEATURE:
<223> OTHER INFORMATION: SED1a-BsrGI-R primer, which is synthesized and
      a DNA sequence

<400> SEQUENCE: 8
gccatctgta cattataaga ataacatagc aacaccag                              38

<210> SEQ ID NO 9
<211> LENGTH: 47
<212> TYPE: DNA
<213> ORGANISM: Artificial Sequence
<220> FEATURE:
<223> OTHER INFORMATION: SED1p-CBA-F primer, which is synthesized and a
      DNA sequence

<400> SEQUENCE: 9
cctcttcgct attacgccag attggatata gaaaattaac gtaaggc                   47

<210> SEQ ID NO 10
<211> LENGTH: 42
<212> TYPE: DNA
<213> ORGANISM: Artificial Sequence
<220> FEATURE:
<223> OTHER INFORMATION: SED1p-CBA-R primer, which is synthesized and a
      DNA sequence

<400> SEQUENCE: 10
ggcaaattga acagttgcat cttaatagag cgaacgtatt tt                         42

<210> SEQ ID NO 11
<211> LENGTH: 40
<212> TYPE: DNA
<213> ORGANISM: Artificial Sequence
<220> FEATURE:
<223> OTHER INFORMATION: pIBGvsp-CBA-F primer, which is synthesized and
      a DNA sequence

<400> SEQUENCE: 11
aatacgttcg ctctattaag atgcaactgt tcaatttgcc                           40

<210> SEQ ID NO 12
<211> LENGTH: 40
<212> TYPE: DNA
<213> ORGANISM: Artificial Sequence
<220> FEATURE:
<223> OTHER INFORMATION: pIBGvsp-CBA-R primer, which is synthesized and
      a DNA sequence

<400> SEQUENCE: 12
gttaattttc tatatccaat ctggcgtaat agcgaagagg                           40

<210> SEQ ID NO 13
<211> LENGTH: 20
<212> TYPE: DNA
<213> ORGANISM: Artificial Sequence
<220> FEATURE:
<223> OTHER INFORMATION: BGL1-NcoI-F primer, which is synthesized and a
      DNA sequence

<400> SEQUENCE: 13
atgcaactgt tcaatttgcc                                                 20

<210> SEQ ID NO 14
<211> LENGTH: 31
```

```
<212> TYPE: DNA
<213> ORGANISM: Artificial Sequence
<220> FEATURE:
<223> OTHER INFORMATION: BGL1-PG-R primer, which is synthesized and a
      DNA sequence

<400> SEQUENCE: 14
gggcccgggc cgggttgca ccttcgggag c                                    31

<210> SEQ ID NO 15
<211> LENGTH: 32
<212> TYPE: DNA
<213> ORGANISM: Artificial Sequence
<220> FEATURE:
<223> OTHER INFORMATION: EGII-NcoI-F primer, which is synthesized and a
      DNA sequence

<400> SEQUENCE: 15
gccatcccat gggtcagcag actgtctggg gc                                  32

<210> SEQ ID NO 16
<211> LENGTH: 33
<212> TYPE: DNA
<213> ORGANISM: Artificial Sequence
<220> FEATURE:
<223> OTHER INFORMATION: EGII-XhoI-R primer, which is synthesized and a
      DNA sequence

<400> SEQUENCE: 16
gccatcctcg agccctttct tgcgagacac gag                                 33

<210> SEQ ID NO 17
<211> LENGTH: 42
<212> TYPE: DNA
<213> ORGANISM: Artificial Sequence
<220> FEATURE:
<223> OTHER INFORMATION: CBHII-CBA-F primer, which is synthesized and a
      DNA sequence

<400> SEQUENCE: 17
ccgcggagat ctccatggct caagcttgct caagcgtctg gg                       42

<210> SEQ ID NO 18
<211> LENGTH: 43
<212> TYPE: DNA
<213> ORGANISM: Artificial Sequence
<220> FEATURE:
<223> OTHER INFORMATION: CBHIIaa-CBA-R primer, which is synthesized and
      a DNA sequence

<400> SEQUENCE: 18
gagcttttgg cgctcgagcc caggaacgat gggtttgcgt ttg                      43

<210> SEQ ID NO 19
<211> LENGTH: 43
<212> TYPE: DNA
<213> ORGANISM: Artificial Sequence
<220> FEATURE:
<223> OTHER INFORMATION: CBHIIsa-CBA-R primer, which is synthesized and
      a DNA sequence

<400> SEQUENCE: 19
gttgataatt tactcgagcc caggaacgat gggtttgcgt ttg                      43

<210> SEQ ID NO 20
<211> LENGTH: 31
<212> TYPE: DNA
```

<213> ORGANISM: Artificial Sequence
<220> FEATURE:
<223> OTHER INFORMATION: AG alpha 1a-PG-F primer, which is synthesized
     and a DNA sequence

<400> SEQUENCE: 20
cccgggcccg ggcccagcgc caaaagctct t                                  31

<210> SEQ ID NO 21
<211> LENGTH: 20
<212> TYPE: DNA
<213> ORGANISM: Artificial Sequence
<220> FEATURE:
<223> OTHER INFORMATION: AG alpha 1a-BsrGI-R primer, which is
     synthesized and a DNA sequence

<400> SEQUENCE: 21
taaaatctgc ggtgagacgg                                               20

<210> SEQ ID NO 22
<211> LENGTH: 41
<212> TYPE: DNA
<213> ORGANISM: Artificial Sequence
<220> FEATURE:
<223> OTHER INFORMATION: SED1a-PG-F primer, which is synthesized and a
     DNA sequence

<400> SEQUENCE: 22
cccgggcccg ggcccaaatt atcaactgtc ctattatctg c                       41

<210> SEQ ID NO 23
<211> LENGTH: 38
<212> TYPE: DNA
<213> ORGANISM: Artificial Sequence
<220> FEATURE:
<223> OTHER INFORMATION: AG alpha 1acb-CBA-F primer, which is
     synthesized and a DNA sequence

<400> SEQUENCE: 23
acgcaaaccc atcgttcctg ggctcgagcg ccaaaagc                           38

<210> SEQ ID NO 24
<211> LENGTH: 37
<212> TYPE: DNA
<213> ORGANISM: Artificial Sequence
<220> FEATURE:
<223> OTHER INFORMATION: pIBGscb-CBA-R primer, which is synthesized and
     a DNA sequence

<400> SEQUENCE: 24
cagacgcttg agcaagcttg agccatggag atctccg                            37

<210> SEQ ID NO 25
<211> LENGTH: 45
<212> TYPE: DNA
<213> ORGANISM: Artificial Sequence
<220> FEATURE:
<223> OTHER INFORMATION: SED1acb-CBA-F primer, which is synthesized and
     a DNA sequence

<400> SEQUENCE: 25
acgcaaaccc atcgttcctg ggctcgagta aattatcaac tgtcc                   45

<210> SEQ ID NO 26
<211> LENGTH: 44
<212> TYPE: DNA
<213> ORGANISM: Artificial Sequence
<220> FEATURE:
<223> OTHER INFORMATION: NCRv-CBA-F primer, which is synthesized and a DNA sequence

<400> SEQUENCE: 26
tgtactgaga gtgcaccata gggaatacct cgtcaaaaca agac      44

<210> SEQ ID NO 27
<211> LENGTH: 47
<212> TYPE: DNA
<213> ORGANISM: Artificial Sequence
<220> FEATURE:
<223> OTHER INFORMATION: NCRleu2-CBA-R primer, which is synthesized and a DNA sequence

<400> SEQUENCE: 27
acctgagtat tcccacagtt gatgtggaaa tataagttat gcaagag      47

<210> SEQ ID NO 28
<211> LENGTH: 44
<212> TYPE: DNA
<213> ORGANISM: Artificial Sequence
<220> FEATURE:
<223> OTHER INFORMATION: LEU2nc-CBA-F primer, which is synthesized and a DNA sequence

<400> SEQUENCE: 28
ataacttata tttccacatc aactgtggga atactcaggt atcg      44

<210> SEQ ID NO 29
<211> LENGTH: 41
<212> TYPE: DNA
<213> ORGANISM: Artificial Sequence
<220> FEATURE:
<223> OTHER INFORMATION: LEU2v-CBA-R primer, which is synthesized and a DNA sequence

<400> SEQUENCE: 29
tttcacaccg catagatccg ctacgtcgta aggccgtttc t      41

<210> SEQ ID NO 30
<211> LENGTH: 43
<212> TYPE: DNA
<213> ORGANISM: Artificial Sequence
<220> FEATURE:
<223> OTHER INFORMATION: pIBGvleu2-CBA-F primer, which is synthesized and a DNA sequence

<400> SEQUENCE: 30
gaaacggcct tacgacgtag cggatctatg cggtgtgaaa tac      43

<210> SEQ ID NO 31
<211> LENGTH: 45
<212> TYPE: DNA
<213> ORGANISM: Artificial Sequence
<220> FEATURE:
<223> OTHER INFORMATION: pIBGvncr-CBA-R primer, which is synthesized and a DNA sequence

<400> SEQUENCE: 31
tgttttgacg aggtattccc tatggtgcac tctcagtaca atctg      45

<210> SEQ ID NO 32
<211> LENGTH: 42
<212> TYPE: DNA
<213> ORGANISM: Artificial Sequence
<220> FEATURE:

```
<223> OTHER INFORMATION: CWP2pv-CBA-F primer, which is synthesized and a
      DNA sequence

<400> SEQUENCE: 32
cctcttcgct attacgccag cgaactgaac tgccttagct cc                          42

<210> SEQ ID NO 33
<211> LENGTH: 48
<212> TYPE: DNA
<213> ORGANISM: Artificial Sequence
<220> FEATURE:
<223> OTHER INFORMATION: CWP2ps-CBA-R primer, which is synthesized and a
      DNA sequence

<400> SEQUENCE: 33
ggcaaattga acagttgcat ttttttttctt gttagtgtgt agcgaatg                   48

<210> SEQ ID NO 34
<211> LENGTH: 40
<212> TYPE: DNA
<213> ORGANISM: Artificial Sequence
<220> FEATURE:
<223> OTHER INFORMATION: pIBGsc2p-CBA-F primer, which is synthesized and
      a DNA sequence

<400> SEQUENCE: 34
acacactaac aagaaaaaaa atgcaactgt tcaatttgcc                             40

<210> SEQ ID NO 35
<211> LENGTH: 40
<212> TYPE: DNA
<213> ORGANISM: Artificial Sequence
<220> FEATURE:
<223> OTHER INFORMATION: pIBGvc2p-CBA-R primer, which is synthesized and
      a DNA sequence

<400> SEQUENCE: 35
agctaaggca gttcagttcg ctggcgtaat agcgaagagg                             40

<210> SEQ ID NO 36
<211> LENGTH: 40
<212> TYPE: DNA
<213> ORGANISM: Artificial Sequence
<220> FEATURE:
<223> OTHER INFORMATION: CWP2a-PG-F primer, which is synthesized and a
      DNA sequence

<400> SEQUENCE: 36
cccgggcccg ggccccaatt ctctactgtc gcttccgttg                             40

<210> SEQ ID NO 37
<211> LENGTH: 35
<212> TYPE: DNA
<213> ORGANISM: Artificial Sequence
<220> FEATURE:
<223> OTHER INFORMATION: CWP2a-BsrGI-R primer, which is synthesized and
      a DNA sequence

<400> SEQUENCE: 37
gccatctgta cattataaca acatagcagc agcag                                  35

<210> SEQ ID NO 38
<211> LENGTH: 3753
<212> TYPE: DNA
<213> ORGANISM: Saccharomyces cerevisiae
<220> FEATURE:
<221> NAME/KEY: CDS
```

<222> LOCATION: (1)..(3753)
<223> OTHER INFORMATION: Ssd1

<400> SEQUENCE: 38

```
atg tct aaa aat agc aac gtt aac aac aat aga tcc caa gag cca aat        48
Met Ser Lys Asn Ser Asn Val Asn Asn Asn Arg Ser Gln Glu Pro Asn
1               5                   10                  15 aac atg ttt gtg caa acc aca gga ggt ggt aaa aac gcc cca aag cag        96
Asn Met Phe Val Gln Thr Thr Gly Gly Gly Lys Asn Ala Pro Lys Gln
            20                  25                  30 att cat gtt gca cac aga cgt tcc caa agt gag ttg aca aat ttg atg       144
Ile His Val Ala His Arg Arg Ser Gln Ser Glu Leu Thr Asn Leu Met
        35                  40                  45 att gaa caa ttc act ttg cag aag cag ttg gag caa gtt caa gca cag       192
Ile Glu Gln Phe Thr Leu Gln Lys Gln Leu Glu Gln Val Gln Ala Gln
    50                  55                  60 cag caa cag ttg atg gct cag caa cag caa ttg gca caa cag aca gga       240
Gln Gln Gln Leu Met Ala Gln Gln Gln Gln Leu Ala Gln Gln Thr Gly
65                  70                  75                  80 caa tac ctg tca gga aat tct ggc tct aac aat cat ttc acg cct caa       288
Gln Tyr Leu Ser Gly Asn Ser Gly Ser Asn Asn His Phe Thr Pro Gln
                85                  90                  95 ccg cct cac cct cat tac aac tca aac ggt aat tca cct ggt atg agt       336
Pro Pro His Pro His Tyr Asn Ser Asn Gly Asn Ser Pro Gly Met Ser
            100                 105                 110 gca ggt ggc agc aga agt aga act cac tcc agg aac aac tcc gga tat       384
Ala Gly Gly Ser Arg Ser Arg Thr His Ser Arg Asn Asn Ser Gly Tyr
        115                 120                 125 tat cat aat tca tat gat aac aat aac aat agc aat aat cct ggg tct       432
Tyr His Asn Ser Tyr Asp Asn Asn Asn Asn Ser Asn Asn Pro Gly Ser
    130                 135                 140 aac tca cac aga aag acg agt tca caa tcc agc ata tat ggc cat tcc       480
Asn Ser His Arg Lys Thr Ser Ser Gln Ser Ser Ile Tyr Gly His Ser
145                 150                 155                 160 aga aga cat tct tta ggt cta aat gaa gcg aaa aag gct gct gcg gaa       528
Arg Arg His Ser Leu Gly Leu Asn Glu Ala Lys Lys Ala Ala Ala Glu
                165                 170                 175 gaa caa gct aaa aga ata tct ggg ggt gaa gca ggc gta act gtg aag       576
Glu Gln Ala Lys Arg Ile Ser Gly Gly Glu Ala Gly Val Thr Val Lys
            180                 185                 190 ata gat tct gtt caa gct gat agt ggc tca aat tct act aca gaa caa       624
Ile Asp Ser Val Gln Ala Asp Ser Gly Ser Asn Ser Thr Thr Glu Gln
        195                 200                 205 tct gat ttt aaa ttt cca cca cca cca aat gct cat cag ggc cat cgt       672
Ser Asp Phe Lys Phe Pro Pro Pro Pro Asn Ala His Gln Gly His Arg
    210                 215                 220 cgc gca act tca aac cta tca cct ccc tct ttc aaa ttt cct cca aac       720
Arg Ala Thr Ser Asn Leu Ser Pro Pro Ser Phe Lys Phe Pro Pro Asn
225                 230                 235                 240 tct cac ggg gat aat gac gat gaa ttc ata gca acc tct tca acg cac       768
Ser His Gly Asp Asn Asp Asp Glu Phe Ile Ala Thr Ser Ser Thr His
                245                 250                 255 cgc cgt tca aag aca aga aac aat gaa tat tct cca ggc att aat tcc       816
Arg Arg Ser Lys Thr Arg Asn Asn Glu Tyr Ser Pro Gly Ile Asn Ser
            260                 265                 270 aac tgg aga aac caa tca cag caa cct caa cag cag ctt tct cca ttc       864
Asn Trp Arg Asn Gln Ser Gln Gln Pro Gln Gln Gln Leu Ser Pro Phe
        275                 280                 285 cgc cac aga gga tct aat tca agg gat tac aat tcc ttc aat acc tta       912
Arg His Arg Gly Ser Asn Ser Arg Asp Tyr Asn Ser Phe Asn Thr Leu
```

-continued

```
          290                 295                 300
gaa cct cct gcg ata ttt cag cag gga cac aaa cat cgt gcc tct aat      960
Glu Pro Pro Ala Ile Phe Gln Gln Gly His Lys His Arg Ala Ser Asn
305                 310                 315                 320 tca tca gtt cat agt ttc agt tca caa ggt aat aat aac gga ggt gga     1008
Ser Ser Val His Ser Phe Ser Ser Gln Gly Asn Asn Asn Gly Gly Gly
                325                 330                 335 cgt aag tcc cta ttt gca ccc tac ctt ccc caa gcc aac att cca gag     1056
Arg Lys Ser Leu Phe Ala Pro Tyr Leu Pro Gln Ala Asn Ile Pro Glu
            340                 345                 350 cta atc caa gaa ggg aga cta gta gct ggt ata tta aga gtt aat aaa     1104
Leu Ile Gln Glu Gly Arg Leu Val Ala Gly Ile Leu Arg Val Asn Lys
        355                 360                 365 aag aat aga tcg gat gcc tgg gtc tct aca gat ggc gct ctt gat gcg     1152
Lys Asn Arg Ser Asp Ala Trp Val Ser Thr Asp Gly Ala Leu Asp Ala
    370                 375                 380 gat att tac att tgc ggc tcc aaa gat cgt aat aga gca ctt gaa ggt     1200
Asp Ile Tyr Ile Cys Gly Ser Lys Asp Arg Asn Arg Ala Leu Glu Gly
385                 390                 395                 400 gat tta gtc gcg gta gaa cta tta gtt gtg gac gat gtt tgg gag tcc     1248
Asp Leu Val Ala Val Glu Leu Leu Val Val Asp Asp Val Trp Glu Ser
                405                 410                 415 aag aaa gaa aag gaa gaa aag aag agg aga aag gat gcc tct atg caa     1296
Lys Lys Glu Lys Glu Glu Lys Lys Arg Arg Lys Asp Ala Ser Met Gln
            420                 425                 430 cac gat cta att cct ttg aac agt agt gac gat tac cac aac gat gca     1344
His Asp Leu Ile Pro Leu Asn Ser Ser Asp Asp Tyr His Asn Asp Ala
        435                 440                 445 tct gtt act gct gca aca agc aac aat ttt cta tct tct ccc tcc tcg     1392
Ser Val Thr Ala Ala Thr Ser Asn Asn Phe Leu Ser Ser Pro Ser Ser
    450                 455                 460 tct gat tcg cta agc aag gat gat tta tcc gtc aga aga aag agg tca     1440
Ser Asp Ser Leu Ser Lys Asp Asp Leu Ser Val Arg Arg Lys Arg Ser
465                 470                 475                 480 tct act atc aat aat gat agt gat tcc tta tca tct cct acc aaa tca     1488
Ser Thr Ile Asn Asn Asp Ser Asp Ser Leu Ser Ser Pro Thr Lys Ser
                485                 490                 495 gga gta agg aga aga agt tca ttg aaa caa cgt cca act caa aag aaa     1536
Gly Val Arg Arg Arg Ser Ser Leu Lys Gln Arg Pro Thr Gln Lys Lys
            500                 505                 510 aat gac gat gtt gaa gtt gaa ggt cag tca ttg tta tta gtt gaa gaa     1584
Asn Asp Asp Val Glu Val Glu Gly Gln Ser Leu Leu Leu Val Glu Glu
        515                 520                 525 gaa gaa atc aac gat aaa tat aag cca ctt tac gca ggc cat gtc gtt     1632
Glu Glu Ile Asn Asp Lys Tyr Lys Pro Leu Tyr Ala Gly His Val Val
    530                 535                 540 gct gtt ttg gac cgt atc cct ggt cag tta ttt agc ggt aca tta ggt     1680
Ala Val Leu Asp Arg Ile Pro Gly Gln Leu Phe Ser Gly Thr Leu Gly
545                 550                 555                 560 ttg ttg aga cca tcc caa caa gct aat agc gac aat aac aaa cca cca     1728
Leu Leu Arg Pro Ser Gln Gln Ala Asn Ser Asp Asn Asn Lys Pro Pro
                565                 570                 575 caa agc cca aaa att gct tgg ttc aag cct act gat aag aag gtg cca     1776
Gln Ser Pro Lys Ile Ala Trp Phe Lys Pro Thr Asp Lys Lys Val Pro
            580                 585                 590 tta att gca att cct aca gaa tta gct cca aag gac ttt gtt gaa aac     1824
Leu Ile Ala Ile Pro Thr Glu Leu Ala Pro Lys Asp Phe Val Glu Asn
        595                 600                 605 gct gat aaa tac tcc gaa aag tta ttc gtt gcc tct att aaa cgt tgg     1872
```

```
Ala Asp Lys Tyr Ser Glu Lys Leu Phe Val Ala Ser Ile Lys Arg Trp
    610             615                 620 cca atc aca tct ttg cat cca ttt ggt att tta gtt tcc gaa ctt gga      1920
Pro Ile Thr Ser Leu His Pro Phe Gly Ile Leu Val Ser Glu Leu Gly
625                 630                 635                 640 gat att cac gat cct gat act gaa att gat tcc att tta agg gat aac      1968
Asp Ile His Asp Pro Asp Thr Glu Ile Asp Ser Ile Leu Arg Asp Asn
            645                 650                 655 aat ttt ctt tcg aat gaa tat ttg gat caa aaa aat ccg caa aaa gaa      2016
Asn Phe Leu Ser Asn Glu Tyr Leu Asp Gln Lys Asn Pro Gln Lys Glu
        660                 665                 670 aaa cca agt ttt cag ccg cta cca tta acg gct gaa agt cta gaa tat      2064
Lys Pro Ser Phe Gln Pro Leu Pro Leu Thr Ala Glu Ser Leu Glu Tyr
    675                 680                 685 agg agg aat ttt acg gac act aat gag tac aat atc ttt gca att tcc      2112
Arg Arg Asn Phe Thr Asp Thr Asn Glu Tyr Asn Ile Phe Ala Ile Ser
690                 695                 700 gag ctt gga tgg gtg tct gaa ttt gcc tta cat gtc agg aat aac gga      2160
Glu Leu Gly Trp Val Ser Glu Phe Ala Leu His Val Arg Asn Asn Gly
705                 710                 715                 720 aat ggt acc cta gag ctg ggt tgt cat gtt gtt gat gtg acc agc cat      2208
Asn Gly Thr Leu Glu Leu Gly Cys His Val Val Asp Val Thr Ser His
            725                 730                 735 att gaa gaa ggc tcc tct gtt gat agg cgt gcg aga aag agg tcc tct      2256
Ile Glu Glu Gly Ser Ser Val Asp Arg Arg Ala Arg Lys Arg Ser Ser
        740                 745                 750 gcg gtg ttc atg cca caa aaa ctt gtc aat tta tta cca caa tcg ttc      2304
Ala Val Phe Met Pro Gln Lys Leu Val Asn Leu Leu Pro Gln Ser Phe
    755                 760                 765 aac gac gaa ctg tcg ttg gcc cct ggc aag gaa tca gcc acg ctg tcg      2352
Asn Asp Glu Leu Ser Leu Ala Pro Gly Lys Glu Ser Ala Thr Leu Ser
770                 775                 780 gtt gtt tac act cta gac tca tct act tta agg att aaa tct act tgg      2400
Val Val Tyr Thr Leu Asp Ser Ser Thr Leu Arg Ile Lys Ser Thr Trp
785                 790                 795                 800 gta ggc gaa tct aca att tcc ccc tca aac atc ttg tct tta gaa caa      2448
Val Gly Glu Ser Thr Ile Ser Pro Ser Asn Ile Leu Ser Leu Glu Gln
            805                 810                 815 tta gac gaa aaa tta tct act gga agt ccc act agc tac ctc tct act      2496
Leu Asp Glu Lys Leu Ser Thr Gly Ser Pro Thr Ser Tyr Leu Ser Thr
        820                 825                 830 gta cag gaa att gct aga tca ttt tat gct aga aga ata aat gat cca      2544
Val Gln Glu Ile Ala Arg Ser Phe Tyr Ala Arg Arg Ile Asn Asp Pro
    835                 840                 845 gaa gct aca tta ctt ccc acc ctg tcc tta ttg gaa agc ttg gat gac      2592
Glu Ala Thr Leu Leu Pro Thr Leu Ser Leu Leu Glu Ser Leu Asp Asp
850                 855                 860 gaa aaa gtt aag gtt gac ttg aac atc ctg gat aga act tta ggc ttt      2640
Glu Lys Val Lys Val Asp Leu Asn Ile Leu Asp Arg Thr Leu Gly Phe
865                 870                 875                 880 gtt gta att aat gag att aaa aga aag gtc aac tcc act gtt gca gag      2688
Val Val Ile Asn Glu Ile Lys Arg Lys Val Asn Ser Thr Val Ala Glu
            885                 890                 895 aaa att tac acc aaa ctt ggt gat cta gct ctt ttg aga agg cag atg      2736
Lys Ile Tyr Thr Lys Leu Gly Asp Leu Ala Leu Leu Arg Arg Gln Met
        900                 905                 910 caa ccc att gca acc aag atg gcg tca ttt aga aag aaa att caa aat      2784
Gln Pro Ile Ala Thr Lys Met Ala Ser Phe Arg Lys Lys Ile Gln Asn
    915                 920                 925
```

```
ttt ggt tac aat ttt gat acc aat acg gcg gat gaa tta atc aaa ggg      2832
Phe Gly Tyr Asn Phe Asp Thr Asn Thr Ala Asp Glu Leu Ile Lys Gly
        930             935             940 gtg cta aaa att aaa gat gac gat gtt aga gtc gga att gaa att tta      2880
Val Leu Lys Ile Lys Asp Asp Asp Val Arg Val Gly Ile Glu Ile Leu
945             950             955             960 ctg ttt aaa acc atg cca aga gct aga tac ttt att gct ggc aaa gta      2928
Leu Phe Lys Thr Met Pro Arg Ala Arg Tyr Phe Ile Ala Gly Lys Val
            965             970             975 gac ccg gac caa tat ggg cat tat gcc ttg aac cta cct atc tac aca      2976
Asp Pro Asp Gln Tyr Gly His Tyr Ala Leu Asn Leu Pro Ile Tyr Thr
        980             985             990 cat ttc aca gcg cca atg aga aga tac gct gat cat gtc gtt cat agg      3024
His Phe Thr Ala Pro Met Arg Arg Tyr Ala Asp His Val Val His Arg
            995             1000            1005 caa tta aag gcc gtt atc cac gat act cca tac acc gaa gat atg          3069
Gln Leu Lys Ala Val Ile His Asp Thr Pro Tyr Thr Glu Asp Met
    1010            1015            1020 gaa gct ttg aag att acc tcc gaa tat tgt aat ttt aaa aag gac          3114
Glu Ala Leu Lys Ile Thr Ser Glu Tyr Cys Asn Phe Lys Lys Asp
1025            1030            1035 tgt gct tat caa gca cag gaa caa gca att cat cta ttg ttg tgt          3159
Cys Ala Tyr Gln Ala Gln Glu Gln Ala Ile His Leu Leu Leu Cys
    1040            1045            1050 aaa aca atc aac gac atg gga aat act aca gga caa tta tta aca          3204
Lys Thr Ile Asn Asp Met Gly Asn Thr Thr Gly Gln Leu Leu Thr
1055            1060            1065 atg gct act gtc tta caa gtt tac gag tcc tcc ttt gat gta ttt          3249
Met Ala Thr Val Leu Gln Val Tyr Glu Ser Ser Phe Asp Val Phe
    1070            1075            1080 att cca gaa ttt ggt att gaa aag aga gtt cat gga gat caa cta          3294
Ile Pro Glu Phe Gly Ile Glu Lys Arg Val His Gly Asp Gln Leu
1085            1090            1095 cct ttg atc aaa gct gag ttt gat ggt acc aat cgt gtc ttg gaa          3339
Pro Leu Ile Lys Ala Glu Phe Asp Gly Thr Asn Arg Val Leu Glu
    1100            1105            1110 ttg cat tgg cag ccc ggc gta gat agt gca act ttt ata cca gca          3384
Leu His Trp Gln Pro Gly Val Asp Ser Ala Thr Phe Ile Pro Ala
1115            1120            1125 gat gaa aaa aat cca aaa tcc tat aga aat tcc att aag aac aaa          3429
Asp Glu Lys Asn Pro Lys Ser Tyr Arg Asn Ser Ile Lys Asn Lys
    1130            1135            1140 ttc aga tcc aca gcc gct gag att gcg aat att gaa cta gat aaa          3474
Phe Arg Ser Thr Ala Ala Glu Ile Ala Asn Ile Glu Leu Asp Lys
1145            1150            1155 gaa gcg gaa tct gaa cca ttg atc agc gat cca ttg agt aag gaa          3519
Glu Ala Glu Ser Glu Pro Leu Ile Ser Asp Pro Leu Ser Lys Glu
    1160            1165            1170 ctc agc gat ttg cat cta aca gta cca aat tta agg cta cca tct          3564
Leu Ser Asp Leu His Leu Thr Val Pro Asn Leu Arg Leu Pro Ser
1175            1180            1185 gca agc gac aac aag caa aat gct tta gaa aaa ttc att tct act          3609
Ala Ser Asp Asn Lys Gln Asn Ala Leu Glu Lys Phe Ile Ser Thr
    1190            1195            1200 act gaa acc aga att gaa aat gat aac tat ata caa gaa ata cat          3654
Thr Glu Thr Arg Ile Glu Asn Asp Asn Tyr Ile Gln Glu Ile His
1205            1210            1215 gaa ttg caa aag att cct att cta ttg aga gct gag gtg ggg atg          3699
Glu Leu Gln Lys Ile Pro Ile Leu Leu Arg Ala Glu Val Gly Met
    1220            1225            1230
```

```
gct ttg cca tgt tta acc gtc cgt gca tta aat cca ttc atg aag        3744
Ala Leu Pro Cys Leu Thr Val Arg Ala Leu Asn Pro Phe Met Lys
    1235                1240                1245 agg gta taa                                                        3753
Arg Val
    1250

<210> SEQ ID NO 39
<211> LENGTH: 1250
<212> TYPE: PRT
<213> ORGANISM: Saccharomyces cerevisiae

<400> SEQUENCE: 39

Met Ser Lys Asn Ser Asn Val Asn Asn Arg Ser Gln Glu Pro Asn
1               5                   10                  15

Asn Met Phe Val Gln Thr Thr Gly Gly Gly Lys Asn Ala Pro Lys Gln
            20                  25                  30

Ile His Val Ala His Arg Arg Ser Gln Ser Glu Leu Thr Asn Leu Met
        35                  40                  45

Ile Glu Gln Phe Thr Leu Gln Lys Gln Leu Glu Gln Val Gln Ala Gln
    50                  55                  60

Gln Gln Gln Leu Met Ala Gln Gln Gln Leu Ala Gln Thr Gly
65                  70                  75                  80

Gln Tyr Leu Ser Gly Asn Ser Gly Ser Asn Asn His Phe Thr Pro Gln
                85                  90                  95

Pro Pro His Pro His Tyr Asn Ser Asn Gly Asn Ser Pro Gly Met Ser
            100                 105                 110

Ala Gly Gly Ser Arg Ser Arg Thr His Ser Arg Asn Asn Ser Gly Tyr
        115                 120                 125

Tyr His Asn Ser Tyr Asp Asn Asn Asn Ser Asn Asn Pro Gly Ser
    130                 135                 140

Asn Ser His Arg Lys Thr Ser Ser Gln Ser Ser Ile Tyr Gly His Ser
145                 150                 155                 160

Arg Arg His Ser Leu Gly Leu Asn Glu Ala Lys Lys Ala Ala Ala Glu
                165                 170                 175

Glu Gln Ala Lys Arg Ile Ser Gly Gly Glu Ala Gly Val Thr Val Lys
            180                 185                 190

Ile Asp Ser Val Gln Ala Asp Ser Gly Ser Asn Ser Thr Thr Glu Gln
        195                 200                 205

Ser Asp Phe Lys Phe Pro Pro Pro Asn Ala His Gln Gly His Arg
    210                 215                 220

Arg Ala Thr Ser Asn Leu Ser Pro Pro Ser Phe Lys Phe Pro Pro Asn
225                 230                 235                 240

Ser His Gly Asp Asn Asp Asp Glu Phe Ile Ala Thr Ser Ser Thr His
                245                 250                 255

Arg Arg Ser Lys Thr Arg Asn Asn Glu Tyr Ser Pro Gly Ile Asn Ser
            260                 265                 270

Asn Trp Arg Asn Gln Ser Gln Gln Pro Gln Gln Gln Leu Ser Pro Phe
        275                 280                 285

Arg His Arg Gly Ser Asn Ser Arg Asp Tyr Asn Ser Phe Asn Thr Leu
    290                 295                 300

Glu Pro Pro Ala Ile Phe Gln Gln Gly His Lys His Arg Ala Ser Asn
305                 310                 315                 320

Ser Ser Val His Ser Phe Ser Ser Gln Gly Asn Asn Gly Gly Gly
                325                 330                 335
```

-continued

```
Arg Lys Ser Leu Phe Ala Pro Tyr Leu Pro Gln Ala Asn Ile Pro Glu
            340                 345                 350

Leu Ile Gln Glu Gly Arg Leu Val Ala Gly Ile Leu Arg Val Asn Lys
            355                 360                 365

Lys Asn Arg Ser Asp Ala Trp Val Ser Thr Asp Gly Ala Leu Asp Ala
            370                 375                 380

Asp Ile Tyr Ile Cys Gly Ser Lys Asp Arg Asn Arg Ala Leu Glu Gly
385                 390                 395                 400

Asp Leu Val Ala Val Glu Leu Val Val Asp Asp Val Trp Glu Ser
                405                 410                 415

Lys Lys Glu Lys Glu Lys Lys Arg Arg Lys Asp Ala Ser Met Gln
            420                 425                 430

His Asp Leu Ile Pro Leu Asn Ser Ser Asp Asp Tyr His Asn Asp Ala
            435                 440                 445

Ser Val Thr Ala Ala Thr Ser Asn Asn Phe Leu Ser Ser Pro Ser Ser
            450                 455                 460

Ser Asp Ser Leu Ser Lys Asp Asp Leu Ser Val Arg Arg Lys Arg Ser
465                 470                 475                 480

Ser Thr Ile Asn Asn Asp Ser Asp Ser Leu Ser Ser Pro Thr Lys Ser
                485                 490                 495

Gly Val Arg Arg Arg Ser Ser Leu Lys Gln Arg Pro Thr Gln Lys Lys
            500                 505                 510

Asn Asp Asp Val Glu Val Glu Gly Gln Ser Leu Leu Leu Val Glu Glu
            515                 520                 525

Glu Glu Ile Asn Asp Lys Tyr Lys Pro Leu Tyr Ala Gly His Val Val
            530                 535                 540

Ala Val Leu Asp Arg Ile Pro Gly Gln Leu Phe Ser Gly Thr Leu Gly
545                 550                 555                 560

Leu Leu Arg Pro Ser Gln Gln Ala Asn Ser Asp Asn Asn Lys Pro Pro
                565                 570                 575

Gln Ser Pro Lys Ile Ala Trp Phe Lys Pro Thr Asp Lys Lys Val Pro
            580                 585                 590

Leu Ile Ala Ile Pro Thr Glu Leu Ala Pro Lys Asp Phe Val Glu Asn
            595                 600                 605

Ala Asp Lys Tyr Ser Glu Lys Leu Phe Val Ala Ser Ile Lys Arg Trp
            610                 615                 620

Pro Ile Thr Ser Leu His Pro Phe Gly Ile Leu Val Ser Glu Leu Gly
625                 630                 635                 640

Asp Ile His Asp Pro Asp Thr Glu Ile Asp Ser Ile Leu Arg Asp Asn
                645                 650                 655

Asn Phe Leu Ser Asn Glu Tyr Leu Asp Gln Lys Asn Pro Gln Lys Glu
            660                 665                 670

Lys Pro Ser Phe Gln Pro Leu Pro Leu Thr Ala Glu Ser Leu Glu Tyr
            675                 680                 685

Arg Arg Asn Phe Thr Asp Thr Asn Glu Tyr Asn Ile Phe Ala Ile Ser
            690                 695                 700

Glu Leu Gly Trp Val Ser Glu Phe Ala Leu His Val Arg Asn Asn Gly
705                 710                 715                 720

Asn Gly Thr Leu Glu Leu Gly Cys His Val Asp Val Thr Ser His
                725                 730                 735

Ile Glu Glu Gly Ser Ser Val Asp Arg Arg Ala Arg Lys Arg Ser Ser
            740                 745                 750
```

-continued

Ala Val Phe Met Pro Gln Lys Leu Val Asn Leu Leu Pro Gln Ser Phe
    755                 760                 765

Asn Asp Glu Leu Ser Leu Ala Pro Gly Lys Glu Ser Ala Thr Leu Ser
    770                 775                 780

Val Val Tyr Thr Leu Asp Ser Ser Thr Leu Arg Ile Lys Ser Thr Trp
785                 790                 795                 800

Val Gly Glu Ser Thr Ile Ser Pro Ser Asn Ile Leu Ser Leu Glu Gln
                805                 810                 815

Leu Asp Glu Lys Leu Ser Thr Gly Ser Pro Thr Ser Tyr Leu Ser Thr
            820                 825                 830

Val Gln Glu Ile Ala Arg Ser Phe Tyr Ala Arg Arg Ile Asn Asp Pro
        835                 840                 845

Glu Ala Thr Leu Leu Pro Thr Leu Ser Leu Leu Glu Ser Leu Asp Asp
    850                 855                 860

Glu Lys Val Lys Val Asp Leu Asn Ile Leu Asp Arg Thr Leu Gly Phe
865                 870                 875                 880

Val Val Ile Asn Glu Ile Lys Arg Lys Val Asn Ser Thr Val Ala Glu
                885                 890                 895

Lys Ile Tyr Thr Lys Leu Gly Asp Leu Ala Leu Leu Arg Arg Gln Met
            900                 905                 910

Gln Pro Ile Ala Thr Lys Met Ala Ser Phe Arg Lys Lys Ile Gln Asn
        915                 920                 925

Phe Gly Tyr Asn Phe Asp Thr Asn Thr Ala Asp Glu Leu Ile Lys Gly
    930                 935                 940

Val Leu Lys Ile Lys Asp Asp Val Arg Val Gly Ile Glu Ile Leu
945                 950                 955                 960

Leu Phe Lys Thr Met Pro Arg Ala Arg Tyr Phe Ile Ala Gly Lys Val
                965                 970                 975

Asp Pro Asp Gln Tyr Gly His Tyr Ala Leu Asn Leu Pro Ile Tyr Thr
            980                 985                 990

His Phe Thr Ala Pro Met Arg Arg Tyr Ala Asp His Val Val His Arg
        995                 1000                1005

Gln Leu Lys Ala Val Ile His Asp Thr Pro Tyr Thr Glu Asp Met
    1010                1015                1020

Glu Ala Leu Lys Ile Thr Ser Glu Tyr Cys Asn Phe Lys Lys Asp
    1025                1030                1035

Cys Ala Tyr Gln Ala Gln Glu Gln Ala Ile His Leu Leu Leu Cys
    1040                1045                1050

Lys Thr Ile Asn Asp Met Gly Asn Thr Thr Gly Gln Leu Leu Thr
    1055                1060                1065

Met Ala Thr Val Leu Gln Val Tyr Glu Ser Ser Phe Asp Val Phe
    1070                1075                1080

Ile Pro Glu Phe Gly Ile Glu Lys Arg Val His Gly Asp Gln Leu
    1085                1090                1095

Pro Leu Ile Lys Ala Glu Phe Asp Gly Thr Asn Arg Val Leu Glu
    1100                1105                1110

Leu His Trp Gln Pro Gly Val Asp Ser Ala Thr Phe Ile Pro Ala
    1115                1120                1125

Asp Glu Lys Asn Pro Lys Ser Tyr Arg Asn Ser Ile Lys Asn Lys
    1130                1135                1140

Phe Arg Ser Thr Ala Ala Glu Ile Ala Asn Ile Glu Leu Asp Lys
    1145                1150                1155

Glu Ala Glu Ser Glu Pro Leu Ile Ser Asp Pro Leu Ser Lys Glu

-continued

```
                        1160                1165                1170

Leu Ser  Asp Leu His Leu Thr  Val Pro Asn Leu Arg  Leu Pro Ser
        1175                1180                1185

Ala Ser  Asp Asn Lys Gln Asn  Ala Leu Glu Lys Phe  Ile Ser Thr
        1190                1195                1200

Thr Glu  Thr Arg Ile Glu Asn  Asp Asn Tyr Ile Gln  Glu Ile His
        1205                1210                1215

Glu Leu  Gln Lys Ile Pro Ile  Leu Leu Arg Ala Glu  Val Gly Met
        1220                1225                1230

Ala Leu  Pro Cys Leu Thr Val  Arg Ala Leu Asn Pro  Phe Met Lys
        1235                1240                1245

Arg Val
    1250
```

<210> SEQ ID NO 40
<211> LENGTH: 55
<212> TYPE: DNA
<213> ORGANISM: Artificial Sequence
<220> FEATURE:
<223> OTHER INFORMATION: SED1d-zeo-F1 primer, which is synthesized and a DNA sequence

<400> SEQUENCE: 40
aagaaaagtt aagggtaatt ttacctattt agcttgcaaa ttaaagccctt cgagc          55

<210> SEQ ID NO 41
<211> LENGTH: 55
<212> TYPE: DNA
<213> ORGANISM: Artificial Sequence
<220> FEATURE:
<223> OTHER INFORMATION: SED1d-zeo-R1 primer, which is synthesized and a DNA sequence

<400> SEQUENCE: 41
taagaaggcg gatgtgtcaa acaccaccgt cccacacacc atagcttcaa aatgt          55

<210> SEQ ID NO 42
<211> LENGTH: 70
<212> TYPE: DNA
<213> ORGANISM: Artificial Sequence
<220> FEATURE:
<223> OTHER INFORMATION: SED1d-zeo-F2 primer, which is synthesized and a DNA sequence

<400> SEQUENCE: 42 cgaaacaat aaaaaatgga aaacgacaa cattccaccc aacaactaca aagaaaagtt       60
aagggtaatt                                                              70

<210> SEQ ID NO 43
<211> LENGTH: 70
<212> TYPE: DNA
<213> ORGANISM: Artificial Sequence
<220> FEATURE:
<223> OTHER INFORMATION: SED1d-zeo-R2 primer, which is synthesized and a DNA sequence

<400> SEQUENCE: 43
gaagtgaaaa acgaataaca aaaaaataac ataatactga aagaaagcat taagaaggcg     60
gatgtgtcaa                                                              70

<210> SEQ ID NO 44
<211> LENGTH: 43

```
<212> TYPE: DNA
<213> ORGANISM: Artificial Sequence
<220> FEATURE:
<223> OTHER INFORMATION: GA-CBA-R primer, which is synthesized and a DNA
      sequence

<400> SEQUENCE: 44
gttgataatt tactcgagcc agcggcaggt gcaccagcct tag                    43

<210> SEQ ID NO 45
<211> LENGTH: 46
<212> TYPE: DNA
<213> ORGANISM: Artificial Sequence
<220> FEATURE:
<223> OTHER INFORMATION: AA-CBA-F primer, which is synthesized and a DNA
      sequence

<400> SEQUENCE: 45
aatacgttcg ctctattaag atgagatttc cttcaattt tactgc                  46

<210> SEQ ID NO 46
<211> LENGTH: 44
<212> TYPE: DNA
<213> ORGANISM: Artificial Sequence
<220> FEATURE:
<223> OTHER INFORMATION: AA-CBA-R primer, which is synthesized and a DNA
      sequence

<400> SEQUENCE: 46
aataggacag ttgataattt cttgtcatcg tcatccttgt agtc                   44

<210> SEQ ID NO 47
<211> LENGTH: 45
<212> TYPE: DNA
<213> ORGANISM: Artificial Sequence
<220> FEATURE:
<223> OTHER INFORMATION: SED1aga-CBA-F primer, which is synthesized and
      a DNA sequence

<400> SEQUENCE: 47
aggctggtgc acctgccgct ggctcgagta aattatcaac tgtcc                  45

<210> SEQ ID NO 48
<211> LENGTH: 47
<212> TYPE: DNA
<213> ORGANISM: Artificial Sequence
<220> FEATURE:
<223> OTHER INFORMATION: SED1aaa-CBA-F primer, which is synthesized and
      a DNA sequence

<400> SEQUENCE: 48
acaaggatga cgatgacaag aaattatcaa ctgtcctatt atctgcc                47

<210> SEQ ID NO 49
<211> LENGTH: 48
<212> TYPE: DNA
<213> ORGANISM: Artificial Sequence
<220> FEATURE:
<223> OTHER INFORMATION: SED1p-CBA-R2 primer, which is synthesized and a
      DNA sequence

<400> SEQUENCE: 49
aaaattgaag gaaatctcat cttaatagag cgaacgtatt ttattttg               48
```

POLYNUCLEOTIDE FOR CELL SURFACE LAYER EXPRESSION

The present application is a National Stage Application of PCT/JP2014/058189, filed Mar. 25, 2014, which claims priority from Japanese Patent Application No. 2013-062795, filed Mar. 25, 2013.

TECHNICAL FIELD

The present invention relates to a polynucleotide for cell surface expression, and more specifically relates to a polynucleotide for cell surface expression that allows for the production of a yeast displaying an enzyme on the cell surface with a high activity.

BACKGROUND ART

Recently, since there is a concern that fossil fuels are being exhausted, alternative fuels have been developed. In particular, bioethanol derived from biomass has attracted attention. This is because biomass is a renewable resource, which exists in large amounts on the earth, and can be used without increasing carbon dioxide in the atmosphere (carbon neutral) so as to contribute to the prevention of global warming.

The attempt has been made that fermentation microorganisms that originally cannot utilize main components of soft biomass, such as cellulose or hemicellulose, are modified by bioengineering procedures to attain ethanol fermentation directly from non-edible carbon sources.

As such bioengineering procedures, cell surface engineering are suitably used. Examples of the cell surface engineering include a method using a GPI anchor protein of a cell surface-localized protein. As such a GPI anchor protein, various proteins are known (Patent Documents 1 to 4 and Non-Patent Documents 1 to 5, for example). Meanwhile, a promoter may be involved in the expression of protein in the cell surface engineering. Examples of known promoters exhibiting a high promoter activity in yeast cells include yeast SED1 promoter, GAPDH promoter, PGK1 promoter, ADH1 promoter, and the like (Patent Documents 2 to 4, for example).

PRIOR ART DOCUMENTS

Patent Documents

Patent Document 1: Japanese Laid-Open Patent Publication No. 2011-160727
Patent Document 2: Japanese Laid-Open Patent Publication No. 2008-86310
Patent Document 3: Japanese Laid-Open Patent Publication No. 2007-189909
Patent Document 4: Japanese Laid-Open Patent Publication No. 2005-245335
Patent Document 5: Japanese Laid-Open Patent Publication No. 2011-30563

Non-Patent Documents

Non-Patent Document 1: Biotechnol. Lett., 2010, vol. 32, pp. 1131-1136
Non-Patent Document 2: Mol. Microbiol., 2004, vol. 52, pp. 1413-1425
Non-Patent Document 3: Appl. Environmen. Microbiol., 1997, vol. 63, pp. 615-620
Non-Patent Document 4: Biotechnol. Lett., 2010, vol. 32, pp. 255-260
Non-Patent Document 5: J. Bacteriol., 1997, vol. 179, pp. 1513-1520
Non-Patent Document 6: Nature Methods, 2009, vol. 6, pp. 343-345
Non-Patent Document 7: Yeast, 1998, vol. 14, pp. 115-132
Non-Patent Document 8: Appl. Microbiol. Biotechnol., 2006, vol. 72, pp. 1136-1143
Non-Patent Document 9: Appl. Microbiol. Biotechnol., 2010, vol. 85, pp. 1491-1498
Non-Patent Document 10: Enzyme Microb. Technol., 2012, vol. 50, pp. 343-347

SUMMARY OF INVENTION

Problems to be Solved by the Invention

It is an object of the present invention to provide a polynucleotide for cell surface expression that allows for the production of a yeast displaying an enzyme on the cell surface with a high activity.

Means for Solving the Problems

The present invention provides a polynucleotide for cell surface expression, comprising: a promoter, a secretion signal sequence, a sequence encoding an intended protein, and a sequence encoding a cell surface-localized protein or a cell membrane-binding domain thereof, wherein the promoter is a promoter of a gene encoding the cell surface-localized protein.

In an embodiment, the cell surface-localized protein is SED1 or CWP2.

The present invention also provides a polynucleotide for cell surface expression, comprising: a promoter, a secretion signal sequence, a sequence encoding an intended protein, and a sequence encoding a cell surface-localized protein or a cell membrane-binding domain thereof, wherein the promoter and the sequence encoding the cell surface-localized protein or the cell membrane-binding domain thereof are derived from any one gene of the genes Sed1 and Cwp2.

In an embodiment, both the promoter and the sequence encoding the cell surface-localized protein or the cell membrane-binding domain thereof are derived from the Sed1 gene; or both the promoter and the sequence encoding the cell surface-localized protein or the cell membrane-binding domain thereof are derived from the Cwp2 gene.

The present invention further provides an expression vector, comprising the polynucleotide for cell surface expression.

The present invention further provides a recombinant yeast into which the polynucleotide for cell surface expression or the expression vector has been introduced.

In an embodiment, the recombinant yeast is obtained from a host yeast in which at least one selected from the group consisting of SED1 and SSD1 is deficient.

In a further embodiment, the recombinant yeast is obtained from a host yeast in which SED1 and SSD1 are deficient.

In an embodiment, the recombinant yeast displays at least one enzyme selected from the group consisting of cellulose-degrading enzymes and starch-degrading enzymes on the cell surface.

The present invention also provides a method for producing ethanol, comprising:

performing fermentation culture of the recombinant yeast mentioned above.

Effects of Invention

According to the present invention, provided is a polynucleotide for cell surface expression that allows for the production of a yeast displaying a protein such as an enzyme on the cell surface with a high activity. The yeast into which such a polynucleotide has been introduced can express a protein on the cell surface with a high activity.

MODE FOR CARRYING OUT THE INVENTION

Figure 1:
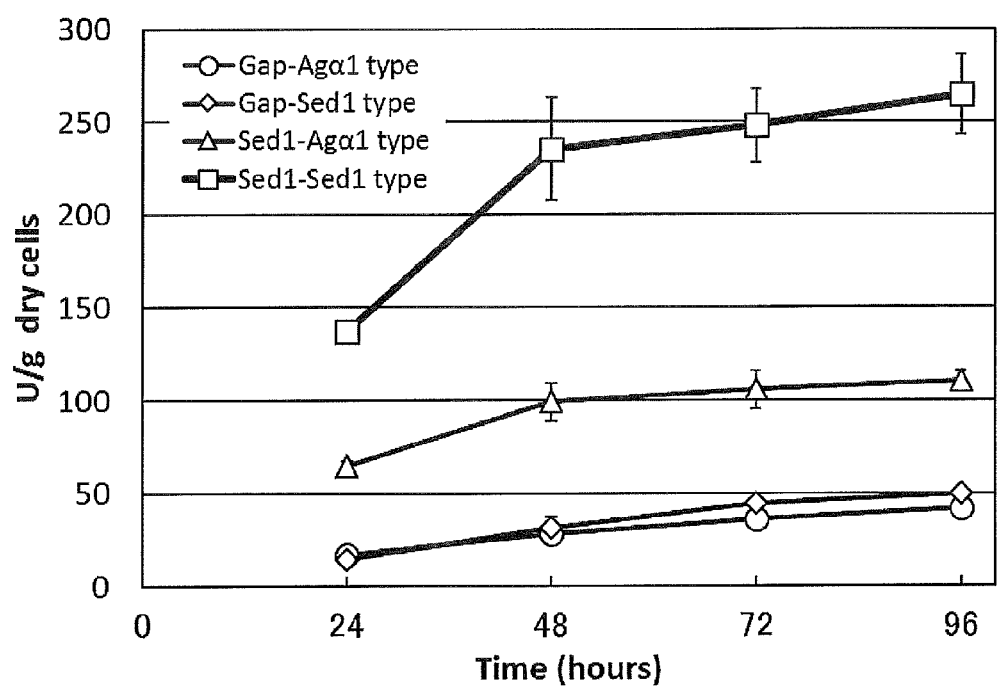
FIG. 1 is a graph showing the time course of a β-glucosidase activity during culture for the Gap-Agα1 recombinant strain, Gap-Sed1 recombinant strain, Sed1-Agα1 recombinant strain, and Sed1-Sed1 recombinant strain for BGL1 gene.

Hereinafter, the present invention will be described in detail.

A polynucleotide for cell surface expression is a polynucleotide including a promoter, a secretion signal sequence, a sequence encoding an intended protein, and a sequence encoding a cell surface-localized protein or a cell membrane-binding domain thereof.

(Cell Surface-Localized Protein and Cell Membrane-Binding Domain Thereof)

"Cell surface-localized protein" refers to a protein anchored, or attached or adhered to the cell surface to be localized therein. Known examples of the cell surface-localized protein include a protein modified with a lipid which is anchored to the cell membrane through a covalent bond with a component of the membrane. Herein, "the cell surface-localized protein and the cell membrane-binding domain thereof" may be collectively referred to simply as an "anchor", based on their roles.

Typical examples of the cell surface-localized protein include a GPI (glycosyl phosphatidyl inositol: glycolipid having, as a basic structure, ethanolamine phosphate-6 mannose α-1,2 mannose α-1,6 mannose α-1,4 glucosamine α-1,6 inositol phospholipid) anchor protein. The GPI anchor protein, which has a glycolipid GPI at its C-terminus, is bound to the surface of a cell membrane through a covalent bond of the GPI with PI (phosphatidyl inositol) in the cell membrane.

The bonding of GPI to the C-terminus of the GPI anchor protein is made as follows. After transcription and translation, the GPI anchor protein is secreted into the lumen of the endoplasmic reticulum by the action of a secretion signal present on the N-terminal side. There is a domain at or near the C-terminus of a GPI anchor protein, and the domain is recognized by a GPI anchor on its binding to the GPI anchor protein, and is called a GPI anchor attachment signal. In the lumen of the endoplasmic reticulum and the Golgi body, the GPI anchor attachment signal domain is cleaved to newly generate C-terminus, and a GPI is bound to the newly generated C-terminus.

The protein bound by the GPI is transported to the cell membrane through secretion vesicles, and is anchored to the cell membrane through a covalent bond of the GPI with PI in the cell membrane. Then, the GPI anchor is cleaved by phosphatidylinositol-dependent phospholipase C (PI-PLC), and is incorporated into the cell wall to display the protein on the cell surface in the state of anchoring to the cell wall.

In the present invention, it is possible to use a polynucleotide encoding a GPI anchor protein which is a cell surface-localized protein, at its entirety or region including a GPI anchor attachment signal domain which is a cell membrane-binding domain thereof. The cell membrane-binding domain (GPI anchor attachment signal domain) is typically a C-terminal region of the cell surface-localized protein. The cell membrane-binding domain may be any region, as long as it includes the GPI anchor attachment signal domain, and may further include any other portion of the GPI anchor protein, as long as it does not inhibit the enzyme activity of the fusion protein.

The GPI anchor protein may be any protein as long as it functions in a yeast cell. Examples of the GPI anchor protein include α- or α-agglutinin (AGα1, AGA1), TIP1, FLO1, SED1, CWP1, and CWP2, and SED1 and CWP2 are preferred.

SED1 is a main cell surface-localized protein in the stationary phase of yeast Saccharomyces cerevisiae, which is considered to be induced by stress and contribute to maintaining the integrity of the cell wall. The gene, Sed1, for SED1 can be obtained, for example, using a method commonly used by those skilled in the art, based on the sequence information registered in GenBank (GenBank accession number NM_001180385; NCBI Gene ID: 851649). The base sequence of the protein coding region of Sed1 is shown in SEQ. ID. No. 1, and the amino acid sequence of the encoded protein is shown in SEQ. ID. No. 2. The cell membrane-binding domain (GPI anchor attachment signal domain) of SED1 is, for example, a region including positions 110 to 338 of SEQ. ID. No. 2. The polynucleotide encoding SED1 may be a polynucleotide encoding a full-length amino acid sequence of SEQ. ID. No. 2, or may be a polynucleotide encoding a partial sequence (e.g., sequence including the amino acid sequence at positions 110 to 338 of SEQ. ID. No. 2), as long as the anchor function is not impaired.

CWP2 is a cell surface-localized protein of yeast *Saccharomyces cerevisiae*. The gene, Cwp2, for CWP2 can be obtained, for example, using a method commonly used by those skilled in the art, based on the sequence information registered in GenBank (GenBank accession number NM_001180025; NCBI Gene ID: 853765). The base sequence of the protein coding region of Cwp2 is shown in SEQ. ID. No. 3, and the amino acid sequence of the encoded protein is shown in SEQ. ID. No. 4. The cell membrane-binding domain (GPI anchor attachment signal domain) of CWP2 is, for example, a region including positions 26 to 92 of SEQ. ID. No. 4. The polynucleotide encoding CWP2 may be a polynucleotide encoding a full-length amino acid sequence of SEQ. ID. No. 4, or may be a polynucleotide encoding a partial sequence (e.g., sequence including the amino acid sequence at positions 26 to 92 of SEQ. ID. No. 4), as long as the anchor function is not impaired.

Herein, the polynucleotide may be a polynucleotide encoding a protein composed of an amino acid sequence in which one or several amino acids are deleted from, substituted with, or added to those in a disclosed amino acid sequence, and substantially having functions or effects desired in the present invention. The number of types of mutations (e.g., deletion, substitution, or addition) of amino acids in the disclosed amino acid sequence may be one, or may be two or more in combination. Furthermore, without any particular limitation, the total number of mutations is, for example, 1 or more and 10 or less, or 1 or more and 5 or less. The amino acid substitution may be any substitution, as long as the functions or effects are substantially maintained, but examples thereof include conservative substitution. The conservative substitution may be specifically substitution in the following groups (i.e., substitution between amino acids shown in each parenthesis): (glycine, alanine), (valine, isoleucine, leucine), (aspartic acid, glutamic acid), (asparagine, glutamine), (serine, threonine), (lysine, arginine), or (phenylalanine, tyrosine).

In another embodiment, the polynucleotide may be a polynucleotide encoding a protein having an amino acid sequence having a sequence identity of, for example, 70% or more, with a disclosed amino acid sequence, and substantially having functions or effects desired in the present invention. The sequence identity in the amino acid sequence may be 74% or more, 78% or more, 80% or more, 85% or more, 90% or more, 92% or more, 95% or more, 98% or more, or 99% or more.

In this specification, the identity or the similarity of sequences is, as known in the art, a relationship between two or more proteins or between two or more polynucleotides determined by comparing the sequences. The "identity" of sequences refers to the degree to what extent protein or polynucleotide sequences are identical to each other, as determined from alignments of the protein or polynucleotide sequences, or, in some cases, from alignments of continuous partial sequences. Furthermore, the "similarity" refers to the degree to what extent protein or polynucleotide sequences are similar to each other, as determined from alignments of the protein or polynucleotide sequences, or, in some cases, from alignments of continuous partial sequences. More specifically, it is determined from the identity and the conservation of sequences (substitution maintaining specific amino acids in the sequences or physicochemical characteristics in the sequences). Note that the similarity is referred to as "Similarity" in a sequence homology search result of BLAST (described later). The method for determining the identity and the similarity is preferably a method designed such that alignments are formed as long as possible between sequences that are to be compared. The method for determining the identity and the similarity is provided as a publicly available program. The identity and the similarity can be determined, for example, the BLAST (Basic Local Alignment Search Tool) program by Altschul et al. (e.g., Altschul et at, J. Mol. Biol., 1990, 215: 403-410; Altschul et al., Nucleic Acids Res., 1997, 25: 3389-3402). There is no particular limitation on the conditions when using software such as the BLAST, but it is preferable to use default values.

In another embodiment, the polynucleotide may be a polynucleotide that hybridizes under stringent conditions with a DNA composed of a base sequence that is complementary to a DNA composed of a disclosed base sequence. The stringent conditions are, for example, a condition under which a so-called specific hybrid is formed and a non-specific hybrid is not formed. For example, it is a condition under which a nucleic acid having a high base sequence identity, that is, a complementary strand of a DNA composed of a base sequence having an identity of, for example, 65% or more, 70% or more, 75% or more, 78% or more, 80% or more, 85% or more, 90% or more, 92% or more, 95% or more, 98% or more, or 99% or more, with a disclosed base sequence hybridizes, and a complementary strand of a nucleic acid having a homology lower than that does not hybridize. More specifically, it is a condition under which the sodium salt concentration is, for example, 15 to 750 mM, 50 to 750 mM, or 300 to 750 mM, the temperature is, for example, 25 to 70° C., 50 to 70° C., or 55 to 65° C., and the formamide concentration is, for example, 0 to 50%, 20 to 50%, or 35 to 45%. Furthermore, under the stringent conditions, the filter washing condition after the hybridization is a condition under which the sodium salt concentration is, for example, 15 to 600 mM, 50 to 600 mM, or 300 to 600 mM, and the temperature is, for example, 50 to 70° C., 55 to 70° C., or 60 to 65° C. The hybridization can be performed using a well known method such as the method described in Sambrook et at, Molecular Cloning, A Laboratory Manual, 3rd Ed, Cold Spring Harbor Laboratory (2001). As the temperature is higher or the salt concentration is lower, the stringency increases, and thus, a polynucleotide having a higher homology can be isolated.

In another embodiment, the polynucleotide may be a polynucleotide having a base sequence having an identity of, for example, 65% or more, 70% or more, 75% or more, 78% or more, 80% or more, 85% or more, 90% or more, 92% or more, 95% or more, 98% or more, or 99% or more, with a disclosed base sequence, and substantially having the functions or effects desired therefor.

For example, in a sequence having: secretion signal sequence-structural gene encoding cell surface-localized protein-sequence encoding GPI anchor attachment recognition signal, the entire or a partial sequence of the structural gene encoding the cell surface-localized protein can be substituted with a sequence encoding an intended protein.

The polynucleotide (gene) encoding the cell surface-localized protein or the cell membrane-binding domain thereof may be obtained from microorganisms having them, for example, by PCR with primers or hybridization with a probe, based on known sequence information. The polynucleotide can be also used by excising it from an existing vector containing the same. Alternatively, the polynucleotide may be synthesized as a nucleic acid fragment using various nucleic acid sequence synthesis methods known in the art, such as chemical synthesis.

(Secretion Signal Sequence)

The "secretion signal sequence" is a polynucleotide sequence encoding a secretion signal peptide.

The secretion signal peptide is a peptide typically linked to the N-terminus of a secretory protein which is secreted out of the cell containing periplasm, and the peptide is similar in structure among organisms, and is, for example, composed of about 20 amino acids, including a sequence of basic amino acids near the N-terminus, followed by rich in hydrophobic amino acids. The secretion signal is typically removed through the degradation by a signal peptidase when the secretory protein is secreted from inside the cell through the cell membrane into the outside of the cell.

In the present invention, any polynucleotide sequence encoding a secretion signal peptide capable of secreting the intended protein out of a yeast cell can be used, and there is no limitation on the origin thereof. Preferable examples thereof include sequences encoding secretion signal peptide of glucoamylase of *Rhizopus oryzae* and the like, secretion signal peptide of glucoamylase of *Aspergillus oryzae*, secretion signal peptide of α- or α-agglutinin of yeast *Saccharomyces cerevisiae*, secretion signal peptide of a factor of yeast *Saccharomyces cerevisiae*, and the like. In particular, in view of secretion efficiency, it is preferable to use the secretion signal peptide sequence of *Rhizopus oryzae*-derived glucoamylase. Also, it is preferable to use the secretion signal peptide sequence of *Aspergillus oryzae*-derived glucoamylase. It is also possible to use a sequence encoding secretion signal peptide originally contained in the intended protein.

(Promoter)

The promoter may be any promoter, as long as it has a promoter activity. The "promoter activity" refers to an activity that allows a transcription factor to be bound to a promoter region, thereby inducing transcription. The promoter may be cut out with a restriction enzyme from, for example, microorganisms or phages having a desired promoter region. The DNA fragment of a promoter region can be obtained by amplifying a desired promoter region by PCR with primers provided with a restriction enzyme recognition site or a site overlapping a cloning vector as necessary. It is also possible to chemically synthesize a desired promoter based on base sequence information of an already known promoter region.

The promoter contained in the polynucleotide for cell surface expression is preferably a promoter of a gene encoding the cell surface-localized protein or the cell membrane-binding domain thereof used as an anchor, or a promoter contained natively in the gene. That is to say, the promoter and the anchor (the cell surface-localized protein or the cell membrane-binding domain thereof) are preferably derived from the same gene.

According to the invention, the promoter used is preferably Sed1 and Cwp2 promoters. The base sequences of the Sed1 and Cwp2 promoters are respectively shown, for example, in *Saccharomyces cerevisiae* S288c chromosome 1V, complete sequence (GenBank accession number NC 001136) and *Saccharomyces cerevisiae* S288c chromosome XI, complete sequence (GenBank accession number NC_001143) of GenBank. The base sequence of the Sed1 and Cwp2 promoters are respectively shown in SEQ. ID. Nos. 5 and 6.

For example, when the cell surface-localized protein is SED1, it is preferable that the coding region of the gene Sed1 therefor is used as a sequence encoding the cell surface-localized protein and the promoter of the gene Sed1 is used as a promoter, and when the cell surface-localized protein is CWP2, it is preferable that the coding region of the gene Cwp2 therefor is used as a sequence encoding the cell surface-localized protein and the promoter of the gene Cwp2 is used as a promoter (in these cases, the promoter and the anchor are derived from the same gene). Meanwhile, the coding region of the gene Cwp2 may be used with the promoter of Sed1, and the coding region of the gene Sed1 may be used with the promoter of Cwp2. The coding regions and the promoters described above may have a base sequence in which one or two or more (e.g., several) nucleotides are mutated (e.g., deleted, added, or substituted) from those in their original base sequence as described above, as long as the intended functions are realized.

(Sequence Encoding Intended Protein)

There is no particular limitation on the type or origin of the intended protein. Examples of the type of the intended protein include enzyme, antibody, ligand, fluorescent protein, and the like. Examples of the enzyme include cellulose-degrading enzyme, starch-degrading enzyme, glycogen-degrading enzyme, xylan-degrading enzyme, chitin-degrading enzyme, lipid-degrading enzyme, and the like, and more specifically include endoglucanase, cellobiohydrolase, β-glucosidase, amylase (e.g., glucoamylase and α-amylase), lipase, and the like.

The polynucleotide sequence encoding the intended protein is preferably a cDNA sequence with no intron.

The polynucleotide sequence encoding the intended protein may be a sequence encoding the full-length, or may be a sequence encoding a partial region of the intended protein, as long as the activity of the intended protein is exhibited. Furthermore, as described above, it may be a base sequence in which one or two or more (e.g., several) nucleotides are mutated (e.g., deleted, added, or substituted), or a base sequence encoding a protein composed of an amino acid sequence in which one or two or more (e.g., several) amino acids are mutated (e.g., deleted, added, or substituted), from those in a base sequence encoding a native protein, as long as the activity of the intended protein is exhibited.

The polynucleotide (gene) encoding the intended protein may be obtained from enzyme-producing microorganisms, for example, by PCR with primers or hybridization with a probe, based on known sequence information. Furthermore, the polynucleotide can be used by excising it, preferably in the form of an expression cassette, from an existing vector containing the polynucleotide encoding the intended protein.

Hereinafter, a description will be given using cellulose-degrading enzymes and starch-degrading enzymes as examples of the intended protein.

The cellulose-degrading enzyme refers to any enzyme that can cleave a β1,4-glycosidic bond. It may be derived from any microorganisms that produce a cellulose-hydrolyzing enzyme. Typical examples of the microorganisms that produce a cellulose-hydrolyzing enzyme include microorganisms belonging to the genus *Aspergillus* (e.g., *Aspergillus aculeatus*, *Aspergillus niger*, and *Aspergillus oryzae*), the genus *Trichoderma* (e.g., *Trichoderma reesei*), the genus *Clostridium* (e.g., *Clostridium thermocellum*), the genus Cellulomonas (e.g., Cellulomonas fimi and Cellulomonas uda), the genus Pseudomonas (e.g., Pseudomonas fluorescence), and the like.

Hereinafter, endoglucanase, cellobiohydrolase, and β-glucosidase will be described as typical cellulose-degrading enzymes, but the cellulose-degrading enzyme is not limited thereto.

Endoglucanase is an enzyme that is usually referred to as cellulase, and it cleaves cellulose from the inside of the molecule to generate glucose, cellobiose, and cello-oligosaccharide ("cellulose molecule inside cleaving"). There are five types of endoglucanase and they are respectively referred to as endoglucanase I, endoglucanase II, endoglucanase III, endoglucanase I\ and endoglucanase V. They are different from each other in terms of amino acid sequences, but commonly have the action of cellulose molecule inside cleaving. For example, Trichoderma reesei-derived endoglucanase (especially endoglucanase II: EGII (Patent Document 5, for example)) may be used, but there is no limitation thereto.

Cellobiohydrolase degrades cellulose from either the reducing terminus or the non-reducing terminus thereof to liberate cellobiose ("cellulose molecule terminal cleaving"). There are two types of cellobiohydrolase and they are respectively referred to as cellobiohydrolase I and cellobiohydrolase II. They are different from each other in terms of amino acid sequences, but commonly have the action of cellulose molecule terminal cleaving. For example, Trichoderma reesei-derived cellobiohydrolase (especially cellobiohydrolase II: CBHII (Patent Document 5, for example)) may be used, but there is no limitation thereto.

β-Glucosidase is an exo-type hydrolytic enzyme that liberates glucose units from the non-reducing terminus of cellulose ("glucose unit cleaving"). β-Glucosidase can cleave a β1,4-glycosidic bond between aglycone or a sugar chain and β-D-glucose, and hydrolyze cellobiose or cello-oligosaccharide, to generate glucose. β-Glucosidase is a typical example of an enzyme that can hydrolyze cellobiose or cello-oligosaccharide. Currently, there is one type of known β-glucosidase and it is referred to as β-glucosidase 1. For example, Aspergillus aculeatus-derived β-glucosidase (especially β-glucosidase 1: BGL1 (Non-Patent Document 8, for example)) may be used, but there is no limitation thereto.

For favorable cellulose hydrolysis, it is preferable to combine enzymes that hydrolyze cellulose in different ways. Various enzymes that hydrolyze cellulose in different ways, such as cellulose molecule inside cleaving, cellulose molecule terminal cleaving, and glucose unit cleaving, may be combined as appropriate. Examples of the enzymes that have the respective ways of hydrolysis include, but are not limited to, endoglucanase, cellobiohydrolase, and β-glucosidase. A combination of enzymes that hydrolyze cellulose in different ways may be selected from the group consisting of, for example, endoglucanase, cellobiohydrolase, and β-glucosidase. Since it is desirable that glucose, which is a constituent sugar of cellulose, is eventually produced, at least one enzyme that can generate glucose is preferably included. Examples of the enzyme that can generate glucose include endoglucanase, in addition to glucose unit cleaving enzyme (e.g., β-glucosidase). For example, β-glucosidase, endoglucanase, and cellobiohydrolase may be displayed on the cell surface in a yeast.

Hereinafter, glucoamylase and α-amylase will be described as typical starch-degrading enzymes, but the starch-degrading enzyme is not limited thereto.

Glucoamylase is officially referred to as glucan 1,4-α-glucosidase, and is also referred to as 1,4-α-D-glucan glucohydrolase, exo 1,4-α-glucosidase, γ-amylase, lysosomal α-glucosidase, or amyloglucosidase. Glucoamylase hydrolyzes an α-1,4-bond at the non-reducing terminus of a sugar chain in an exo manner, to produce one molecule of dextrose. There is also known glucoamylase that cleaves an α-1,6-bond. Examples of the glucoamylase include, but are not limited to, Rhizopus oryzae-derived glucoamylase (Non-Patent Document 9, for example).

α-Amylase is also referred to as 1,4-α-D-glucan glucanohydrolase, or glycogenase, and is an enzyme irregularly cleaves an α-1,4-bond of starch or glycogen to produce polysaccharide, maltose, or oligosaccharide. It is a general enzyme widely distributed in animals, plants, and microorganisms. Examples of the α-amylase include, but are not limited to, Streptococcus bovis-derived α-amylase (Non-Patent Document 10, for example)).

For favorable starch hydrolysis, it is preferable to combine enzymes that hydrolyze starch in different ways. In an embodiment, both α-amylase and glucoamylase can be displayed on the cell surface in a yeast.

(Terminator)

The polynucleotide for cell surface expression may further include a terminator.

The terminator may be any terminator, as long as it has a terminator activity. The "terminator activity" refers to an activity that terminates transcription in a terminator region. The terminator may be any terminator, as long as it has a terminator activity, and may be cut out with a restriction enzyme from, for example, microorganisms or phages having a desired terminator region. The DNA fragment of a terminator region can be obtained by amplifying a desired terminator region by PCR with primers provided with a restriction enzyme recognition site or a site overlapping a cloning vector as necessary. It is also possible to chemically synthesize a desired terminator based on base sequence information of an already known terminator region.

Examples of the terminator include α-agglutinin terminator, ADH1 (aldehyde dehydrogenase) terminator, GAPDH (glyceraldehyde-3'-phosphate dehydrogenase) terminator, and the like.

(Construction of Polynucleotide for Cell Surface Expression)

A sequence encoding the anchor (the cell surface-localized protein or the cell membrane-binding domain thereof) is ligated to a sequence encoding the intended protein (structural gene), together with the secretion signal sequence in a desired arrangement, and the ligate is arranged downstream of the promoter. These sequences are arranged in the polynucleotide for cell surface expression such that, for example, the intended protein is linked to the N-terminus of the anchor (the cell surface-localized protein or the cell membrane-binding domain thereof) when the intended protein is expressed. That is to say, the sequence encoding the intended protein is positioned on the 5' side of the sequence encoding the anchor. Furthermore, the sequence encoding the intended protein is arranged downstream of the secretion signal sequence.

The terminator can be arranged downstream of the ligate of the above-described factors (the promoter, the secretion signal sequence, the sequence encoding the intended protein, and the sequence encoding the anchor).

The synthesis and the binding of DNAs having the various sequences described above may be performed using a method commonly used by those skilled in the art. For example, the binding of the secretion signal sequence and the structural gene of the intended protein can be carried out by way of site specific mutation or one-step isothermal assembly (Non-Patent Document 6). Such a procedure allows for accurately cleaving a secretion signal sequence and expressing an active enzyme.

Also, the region (structural gene) encoding the intended protein (e.g., endoglucanase, cellobiohydrolase, or β-glucosidase), the secretion signal, and the expression regulatory sequences such as the promoter and the terminator can be excised as appropriate in a form suitable for vector preparation from a known plasmid containing them, and an insert can be prepared together with the sequence encoding the cell surface-localized protein or the cell membrane-binding domain thereof.

(Expression Vector)

The expression vector may be a plasmid vector, or may be an artificial chromosome. If a yeast is used as a host, the vector is preferably in the form of a plasmid because a vector can be easily prepared and a yeast cell can be easily transformed. In order to simplify the procedure for obtaining a DNA, the vector is preferably a yeast—*Escherichia coli* shuttle vector. As necessary, the vector may contain regulatory sequences (operator, enhancer, etc.). Such a vector has, for example, a replication origin (Ori) of a 2 μm plasmid of a yeast and a replication origin of ColE1, as well as a yeast selectable marker (described below) and an *Escherichia coli* selectable marker (drug-resistant gene, etc.).

As the yeast selectable marker, any known markers may be used. Examples thereof include drug-resistant genes, and auxotrophic marker genes (e.g., a gene encoding imidazoleglycerol-phosphate dehydrogenase (HIS3), a gene encoding beta-isopropyl-malate dehydrogenase (LEU2), a gene encoding tryptophan synthase (TRP5), a gene encoding argininosuccinate lyase (ARG4), a gene encoding N-(5'-phosphoribosyl) anthranilate isomerase (TRP1), a gene encoding histidinol dehydrogenase (HIS4), a gene encoding orotidine-5-phosphate decarboxylase (URA3), a gene encoding dihydroorotate dehydrogenase (URA1), a gene encoding galactokinase (GAL1), a gene encoding alpha-aminoadipate reductase (LYS2), etc.). For example, auxotrophic marker genes (e.g., HIS3, LEU2, URA1, TRP1 deficient markers, etc.) may be preferably used.

(Yeast)

There is no particular limitation on the yeast that is used as a host, as long as it belongs to *Ascomycetous* yeasts. Of these, yeasts belonging to Saccharomycetaceae are preferable, and yeasts belonging to *Saccharomyces* are more preferable.

The yeast of the present invention is obtained by introducing the polynucleotide or the expression vector of the present invention to a host yeast. To "introduce" include not only to introduce a gene intended to be expressed in the polynucleotide or the expression vector into a host cell but also to allow it to be expressed in the host cell. There is no particular limitation on the procedure of introducing, and known procedures may be used. Typical examples thereof include transforming a yeast with the expression vector of the present invention as described above. There is no particular limitation on the procedure of transformation, and known procedures, such as transfection such as calcium phosphate treatment, electroporation, lipofection, DEAE dextran treatment, lithium acetate treatment, or protoplast, or microinjection may be used without limit. The introduced gene may be present in the form of a plasmid, or may be present in the form inserted into a yeast chromosome or in the form incorporated into a yeast chromosome by homologous recombination.

The yeast into which the polynucleotide of the present invention has been introduced can be selected according to a common procedure, using, as an indicator, for example, the character by the yeast selectable marker or the activity of the intended protein.

Furthermore, it is possible to see that the intended protein is anchored to the cell surface (displayed on the cell surface) of the obtained yeast according to a common procedure. Examples thereof include action of an antibody against this protein and a fluorescence-labeled secondary antibody such as FITC or an enzyme-labeled secondary antibody such as alkaline phosphatase on a yeast subject; reaction of an antibody against this protein and a biotin-labeled secondary antibody with a yeast subject, and then a fluorescence-labeled streptavidin; and the like.

It is also possible to transform a yeast so as to express multiproteins on the cell surface. In this case, a plurality of expression vectors containing respective gene expression cassettes for sequences encoding multiproteins may be constructed, or a plurality of gene expression cassettes may be placed in one expression vector. For example, δ integration may be used (Patent Document 5).

In an embodiment, for example, a yeast in which at least one selected from the group consisting of SED1 and SSD1 is deficient is used as a host for transformation. The host is preferably a SED1 deficient yeast, and more preferably a SED1 and SSD1 double-deficient yeast. The SED1 is as described above. The SSD1 is a negative regulator to a yeast stress responsive gene, such as SED1. The NCBI gene registration number for a gene for SSD1 is NCBI Gene ID: 851887 (Genbank accession number NM_001180601.1). The base sequence of the gene for SSD1 derived from *Saccharomyces cerevisiae* and the encoded amino acid sequence thereby are respectively shown in SEQ. ID. Nos. 38 and 39.

The yeast in which at least one selected from the group consisting of SED1 and SSD1 is deficient can be obtained, for example, by disrupting, or suppressing expression of, genes encoding these proteins in the host yeast. Examples of such "deficiency" include suppressing the amount of normal protein produced, and producing or facilitating dysfunctional mutant proteins. Examples of the gene manipulation therefor include transgenesis, gene knockout, and knockin. In an embodiment, for example, the SED1 and SSD1 double-deficient yeast is a double-disrupted strain in which both the genes for SED1 and SSD1 are disrupted.

Such deficient yeasts may be produced by preparing primers and the like as appropriate based on known gene sequence information and performing the gene manipulation as mentioned above or may be commercially available deficient strains. Examples of such commercially available deficient strains include Yeast Knockout Collection (available from Open Biosystems) for yeast *Saccharomyces cerevisiae* BY4741 strain (MATα his3 leu2 met15 ura3 strain), and the like.

(Method for Producing Ethanol)

The yeast displaying at least one enzyme selected from the group consisting of cellulose-degrading enzymes and starch-degrading enzymes on the cell surface according to the present invention can be used for ethanol production. In an embodiment, it is a yeast displaying at least one enzyme selected from the group consisting of endoglucanase, cellobiohydrolase, and β-glucosidase on the cell surface (alternatively referred to as "cellulase-displaying yeast" herein). Such a yeast may be a yeast displaying two types of enzymes selected from the group consisting of endoglucanase, cellobiohydrolase, and β-glucosidase; or endoglucanase, cellobiohydrolase, and β-glucosidase on the cell surface. In another embodiment, it is a yeast displaying α-amylase and/or glucoamylase on the cell surface (alternatively referred to as "amylase-displaying yeast" herein). The yeast may display both a cellulose-degrading enzyme and a starch-degrading enzyme on the cell surface. It is preferable to use a cassette containing the coding region of the gene Sed1 and the promoter of the gene Sed1, as a cell surface expression cassette.

The cellulase-displaying yeast may use cellulose and a saccharified product thereof, as a fermentation substrate. The cellulase-displaying yeast may use starch and a saccharified product thereof, as a fermentation substrate. Examples of the obtaining source or the material of the fermentation substrate containing cellulose and a saccharified product thereof and the fermentation substrate containing starch and a saccharified product thereof include biomass. The biomass refers to industrial resources that are not exhaustible resources and are derived from biological materials of recently living organisms. That is to say, biomass refers to renewable organic resources derived from organism, excluding fossil resources. Biomass may include cellulose and/or starch. There is no particular limitation on the biomass, and examples thereof include resource crops and wastes thereof. There is no particular limitation on the resource crops, and examples thereof include corn and sugarcane. Examples of the wastes of resource crops include wastes generated when processing these resource crops. The use of lignocellulosic biomass is preferable because it does not compete with food. There is no particular limitation on the lignocellulosic biomass, and examples thereof include portions (e.g., chaff, roots, stems, and leaves) excluding edible portions of Poaceae plants such as *Oryza sativa*, wheat, *Miscanthus sinensis; Phragmites communis*, and the like, and wastes generated from product of these portions.

As necessary, before fermentation, the fermentation substrate material (e.g., biomass) may be subjected to pre-treatment. With such pre-treatment, polysaccharide (e.g., cellulose and/or starch) in biomass can be degraded through "saccharification" into oligosaccharide or monosaccharide. There is no particular limitation on the pre-treatment process, but examples thereof include enzymatic process, diluted sulfuric acid process, and hydrothermal decomposition process. In view of the cost, diluted sulfuric acid process and hydrothermal process are preferable. In diluted sulfuric acid process, for example, the material is treated with 1 to 5% (v/v) of diluted sulfuric acid at 180 to 200° C. for about 5 minutes to 1 hours. In hydrothermal process, for example, the material is treated with water at 130 to 300° C. at about 10 MPa.

The cell surface displaying yeast can be cultured under aerobic conditions before fermentation, to increase the number of cells. The recombinant yeast can be cultured as appropriate using a method well known to those skilled in the art. The pH of the medium is, for example, 4 to 6, and preferably 5. During aerobic culture, the dissolved oxygen concentration in the medium is, for example, 0.5 to 6 ppm, preferably 1 to 4 ppm, and more preferably 2 ppm. The culture temperature is, for example, 20 to 45° C., preferably 25 to 35° C., and more preferably 30° C. The culture is preferably performed until the number of yeast cells is, for example, 10 g (wet weight)/L or more, preferably 12.5 g (wet weight)/L, and more preferably 15 g (wet weight)/L or more, and the culture time is, for example, about 24 to 96 hours.

During fermentation culture, culturing conditions typically applied to yeasts may be selected and used as appropriate. Typically, in culture for fermentation, stationary culture, shaking culture, aerated and stirred culture, or the like may be used. The aeration condition can be selected as appropriate from anaerobic condition, microaerobic condition, aerobic condition, and the like. The culture temperature is, for example, 25 to 45° C., preferably 30 to 40° C., and more preferably 35° C. The culture time may be set to any time as necessary, and may be, for example, in a range of 24 to 120 hours. The pH can be adjusted using an inorganic or organic acid, an alkaline solution, or the like. The fermentation medium may contain medium components that may be added for culturing yeasts, as necessary, in addition to the fermentation substrate.

After the end of the ethanol fermentation, a process of collecting an ethanol-containing fraction from the culture solution (fermentation liquor) and also a process of purifying or concentrating the fraction may be performed. These processes and means necessary therefor are selected as appropriate by those skilled in the art.

EXAMPLES

Hereinafter, the present invention will be described by way of examples, but the present invention is not limited thereto.

The yeast *Saccharomyces cerevisiae* BY4741 strain (Non-Patent Document 7) used in the examples was obtained from Invitrogen.

All PCR procedures shown in the examples were performed using KOD-Plus-Neo-DNA polymerase (manufactured by Toyobo Co., Ltd.).

All gene introductions into yeasts shown in the examples were performed by lithium acetate treatment procedure.

Example 1: Reparation of Vector Containing Expression Cassette for Cell Surface Display and Vector for Cellulase-Displaying A DNA fragment containing the coding region of *Saccharomyces cerevisiae*-derived cell surface-localized protein gene Sed1 (hereinafter, alternatively referred to as "SED1" for the sake of convenience) was prepared through amplification by PCR using a genome of *Saccharomyces cerevisiae* BY4741 strain as a template with a primer pair (SED1α-XhoI-F (SEQ. ID. No. 7) and SED1α-BsrGI-R (SEQ. ID. No. 8)). This fragment was treated with XhoI and BsrGI, and was ligated to a vector plasmid pIBG13 (vector for cell surface expression (Non-Patent Document 8) having an auxotrophic marker gene HIS3 and a BGL1 expression cassette (i.e., cassette in which a GAPDH (glyceraldehyde-3'-phosphate dehydrogenase) promoter, a secretion signal peptide sequence of *Rhizopus oryzae*-derived glucoamylase, the coding region of BGL1, a 3' half region of α-agglutinin gene (a region of nucleotide positions 991 to 1953 in the coding region of α-agglutinin gene), and a terminator region 445 bp downstream of the coding region were arranged in this order) treated in a similar manner. The obtained plasmid was named pIBG13S.

A DNA fragment containing the promoter region of *Saccharomyces cerevisiae*-derived cell surface-localized protein gene Sed1 was prepared through amplification by PCR using a genome of *Saccharomyces cerevisiae* BY4741 strain as a template with a primer pair SED1p-CBA-F (SEQ. ID. No. 9) and SED1p-CBA-R (SEQ. ID. No. 10). This fragment was ligated, by one-step isothermal assembly, to a fragment amplified using a vector plasmid pIBG13 as a template with a primer pair pIBGvsp-CBA-F (SEQ. ID. No.

11) and pIBGvsp-CBA-R (SEQ. ID. No. 12). The obtained plasmid was named pISpBG13.

The preparation of *Aspergillus aculeatus*-derived β-glucosidase 1 (BGL1) gene, *Trichoderma reesei*-derived endoglucanase II (EGII) gene, and *Trichoderma reesei*-derived cellobiohydrolase II (CBHII) gene were carried out as set forth below.

Gene fragments of BGL1, EGII, and CBHII genes were prepared by PCR, respectively using pIBG13, pδU-PGAGEGII (a vector for cell surface expression of EGII having a 3' half region of α-agglutinin gene: Patent Document 5), and pδU-PGAGCGHII (a vector for cell surface expression of cellobiohydrolase II having a 3' half region of α-agglutinin gene: Patent Document 5) as templates, with a primer pair (BGL1-NcoI-F (SEQ. ID. No. 13) and BGL1-PG-R (SEQ. ID. No. 14)) for BGL1, a primer pair (EGII-NcoI-F (SEQ. ID. No. 15) and EGII-XhoI-R (SEQ. ID. No. 16)) for EGII, and a primer pair (CBHII-CBA-F (SEQ. ID. No. 17) and CBHIIaa-CBA-R (SEQ. ID. No. 18) (for Agα1 linkage) or CBHII-CBA-F (SEQ. ID. No. 17) and CBHIIsa-CBA-R (SEQ. ID. No. 19) (for SED1 linkage)) for CBHII.

A DNA fragment containing a 3' half region of the coding region of Agα1 gene and a DNA fragment containing the coding region of SED1 gene were prepared through amplification by PCR, respectively using pIBG13 and a genome of *Saccharomyces cerevisiae* BY4741 strain as templates, with a primer pair (AGα1a-PG-F (SEQ. ID. No. 20) and AGα1a-BsrGI-R (SEQ. ID. No. 21)) for Agα1 and a primer pair (SED1α-PG-F (SEQ. ID. No. 22) and SED1α-BsrGI-R (SEQ. ID. No. 8)) for SED1.

DNA fragments (BGL1-Agα1 and BGL1-SED1) in which the DNA fragment containing a 3' half region of the coding region of Aged gene or the DNA fragment containing the coding region of SED1 gene was ligated in-frame downstream of the BGL1 gene fragment were prepared through amplification by PCR using a mixture of the BGL1 gene fragment, and the DNA fragment containing a 3' half region of the coding region of Agα1 gene or the DNA fragment containing the coding region of SED1 gene as a template, with a primer pair (BGL1-NcoI-F (SEQ. ID. No. 13) and AGα1a-BsrGI-R (SEQ. ID. No. 21)) for BGL1-Agα1 and a primer pair (BGL1-NcoI-F (SEQ. ID. No. 13) and SED1α-BsrGI-R (SEQ. ID. No. 8)) for BGL1-SED1.

The BGL1-Agα1 and BGL1-SED1 fragments were treated with NcoI and BsrGI, and were ligated in-frame downstream of the secretion signal in a plasmid pIBG13 treated in a similar manner. The obtained plasmids were respectively named pIBG-PG-Agα1 and pIBG-PG-Sed1.

The EGII gene fragment was treated with NcoI and XhoI, and was ligated in-frame downstream of the secretion signal in a plasmid pIBG13 or pIBG13S treated in a similar manner. The obtained plasmids were respectively named pIEG-Agα1 and pIEG-Sed1.

The CBHII gene fragment for Agα1 linkage or the CBHII gene fragment for SED1 linkage was ligated, by one-step isothermal assembly, to a fragment amplified respectively using a vector plasmid pIBG13 or pIBG13S as a template with a primer pair AGα1acb-CBA-F (SEQ. ID. No. 23) and pIBGscb-CBA-R (SEQ. ID. No. 24), or SED1acb-CBA-F (SEQ. ID. No. 25) and pIBGscb-CBA-R (SEQ. ID. No. 24). The obtained plasmids were named pICB-Agα1 and pICB-Sed1.

BGL1-Agα1, BGL1-SED1, EGII-Agα1, and EGII-Sed1 fragments were prepared by respectively treating pIBG-PG-Agα1, pIBG-PG-Sed1, pIEG-Agα1, and pIEG-Sed1 with NcoI and BsrGI, and were ligated in-frame downstream of the secretion signal in a plasmid pISpBG13 treated in a similar manner. The obtained plasmids were respectively named pISpBG-PG-Agα1, pISpBG-PG-Sed1, pISpEG-Agα1, and pISpEG-Sed1.

A DNA fragment containing the promoter region of SED1 gene was prepared through amplification by PCR using pISpBG13 as a template with a primer pair SED1p-CBA-F (SEQ. ID. No. 9) and SED1p-CBA-R (SEQ. ID. No. 10). This fragment was ligated, by one-step isothermal assembly, to a fragment amplified using a plasmid pICB-Sed1 as a template with a primer pair pIBGvsp-CBA-F (SEQ. ID. No. 11) and pIBGvsp-CBA-R (SEQ. ID. No. 12). The obtained plasmid was named pISpCB-Sed1.

A DNA fragment containing a non-coding region on the genome of *Saccharomyces cerevisiae* was prepared through amplification by PCR using a genome of *Saccharomyces cerevisiae* BY4741 strain as a template with a primer pair NCRv-CBA-F (SEQ. ID. No. 26) and NCRleu2-CBA-R (SEQ. ID. No. 27).

A DNA fragment containing the *Saccharomyces cerevisiae*-derived Leu2 gene was prepared through amplification by PCR using a genome of *Saccharomyces cerevisiae* BY4741 strain as a template with a primer pair LEU2nc-CBA-F (SEQ. ID. No. 28) and LEU2v-CBA-R (SEQ. ID. No. 29).

The DNA fragment containing the non-coding region and the DNA fragment containing the Leu2 gene were ligated, by one-step isothermal assembly, to a fragment amplified using a plasmid pICB-Agα1 as a template with a primer pair pIBGvleu2-CBA-F (SEQ. ID. No. 30) and pIBGvncr-CBA-R (SEQ. ID. No. 31). The obtained plasmid was named pINCCB-Agα1.

The DNA fragment containing the non-coding region and the DNA fragment containing the Leu2 gene were ligated, by one-step isothermal assembly, to a fragment amplified using a plasmid pISpCB-Sed1 as a template with a primer pair pIBGvleu2-CBA-F (SEQ. ID. No. 30) and pIBGvncr-CBA-R (SEQ. ID. No. 31). The obtained plasmid was named pINCCB-Sed1.

A DNA fragment containing the promoter region of *Saccharomyces cerevisiae*-derived cell surface-localized protein gene Cwp2 (hereinafter, alternatively referred to as "CWP2" for the sake of convenience) was prepared through amplification by PCR using a genome of *Saccharomyces cerevisiae* BY4741 strain as a template with a primer pair CWP2pv-CBA-F (SEQ. ID. No. 32) and CWP2ps-CBA-R (SEQ. ID. No. 33). This fragment was ligated, by one-step isothermal assembly, to a fragment amplified using a plasmid pISpBG-PG-Sed1 as a template with a primer pair pIBGsc2p-CBA-F (SEQ. ID. No. 34) and pIBGvc2p-CBA-R (SEQ. ID. No. 35). The obtained plasmid was named pIC2BG-PG-Sed1.

A DNA fragment containing the coding region of *Saccharomyces cerevisiae*-derived cell surface-localized protein gene CWP2 was prepared through amplification by PCR using a genome of *Saccharomyces cerevisiae* BY4741 strain as a template with a primer pair CWP2α-PG-F (SEQ. ID. No. 36) and CWP2α-BsrGI-R (SEQ. ID. No. 37).

A DNA fragment (BGL1-CWP2) in which the DNA fragment containing the coding region of the CWP2 gene was ligated in-frame downstream of the BGL1 gene fragment was prepared through amplification by PCR using a mixture of the BGL1 gene fragment and the DNA fragment containing the coding region of CWP2 gene as a template with a primer pair BGL1-NcoI-F (SEQ. ID. No. 13) and CWP2α-BsrGI-R (SEQ. ID. No. 37).

The BGL1-CWP2 fragment was treated with NcoI and BsrGI, and was ligated in-frame downstream of the secretion signal in plasmids pISpBG-PG-Sed1 and pIC2BG-PG-Sed1 treated in a similar manner. The obtained plasmids were respectively named pISpBG-PG-Cwp2 and pIC2BG-PG-Cwp2.

Example 2: Preparation of Cellulase-Displaying Yeast

A plasmid (pIBG-PG-Agα1 or pIEG-Agα1) for any of BGL1 and EGII genes was treated with NdeI, and was each provided with yeast *Saccharomyces cerevisiae* BY4741 strain (MATα his3 leu2 met15 ura3 strain) to transform the strain by lithium acetate treatment procedure. These recombinant strains are referred to as Gap-Agα1 recombinant strains for respective genes.

A plasmid (pIBG-PG-Sed1 or pIEG-Sed1) for any of BGL1 and EGII genes was treated with NdeI, and was each provided with yeast *Saccharomyces cerevisiae* BY4741 strain (MATα his3 leu2 met15 ura3 strain) to transform the strain by lithium acetate treatment procedure. These recombinant strains are referred to as Gap-Sed1 recombinant strains for respective genes.

A plasmid (pISpBG-PG-Agα1 or pISpEG-Agα1) for any of BGL1 and EGII genes was treated with NdeI, and was each provided with yeast *Saccharomyces cerevisiae* BY4741 strain (MATα his3 leu2 met15 ura3 strain) to transform the strain by lithium acetate treatment procedure. These recombinant strains are referred to as Sed1-Agα1 recombinant strains for respective genes.

A plasmid (pISpBG-PG-Sed1 or pISpEG-Sed1) for any of BGL1 and EGII genes was treated with NdeI, and was each provided with yeast *Saccharomyces cerevisiae* BY4741 strain (MATα his3 leu2 met15 ura3 strain) to transform the strain by lithium acetate treatment procedure. These recombinant strains are referred to as Sed1-Sed1 recombinant strains for respective genes.

A plasmid (pISpBG-PG-Cwp2 or pIC2BG-PG-Cwp2) for BGL1 gene was treated with NdeI, and was each provided with yeast *Saccharomyces cerevisiae* BY4741 strain (MATα his3 leu2 met15 ura3 strain) to transform the strain by lithium acetate treatment procedure. These recombinant strains are referred to as Sed1-Cwp2 and Cwp2-Cwp2 recombinant strains for BGL1 gene, respectively.

A plasmid (pINCCB-Agα1) for CBHII gene was treated with NdeI, and was provided with the Gap-Agα1 recombinant strain (MATα leu2 met15 ura3 strain) for EGII gene to transform the strain by lithium acetate treatment procedure. This recombinant strain is referred to as an EGII-CBHII gene co-expression type Gap-Agα1 recombinant strain.

A plasmid (pINCCB-Sed1) for CBHII gene was treated with NdeI, and was provided with the Sed1-Sed1 recombinant strain (MATα leu2 met15 ura3 strain) for EGII gene to transform the strain by lithium acetate treatment procedure. This recombinant strain is referred to as an EGII-CBHII gene co-expression type Sed1-Sed1 recombinant strain.

A vector plasmid pRS403 (HIS3 yeast expression vector: Agilent Technologies), free from any polynucleotide for cell surface expression, was treated with NdeI, and was provided with yeast *Saccharomyces cerevisiae* BY4741 strain (MATα his3 leu2 met15 ura3 strain) to transform the strain by lithium acetate treatment procedure. This recombinant strain is referred to as an empty vector-introduced strain.

Example 3: Examination for β-Glucosidase Activity, 1

The Gap-Agα1 recombinant strain, Gap-Sed1 recombinant strain, Sed1-Agα1 recombinant strain, and Sed1-Sed1 recombinant strain for BGL1 gene were examined for β-glucosidase (BGL) activity.

Cells were inoculated to 5 mL of SD medium (supplemented with leucine, methionine, and uracil) and cultured at 30° C. and 180 rpm for 18 hours (pre-culture), and then were inoculated to 50 mL of 1×YPD medium (initial $OD_{600}$=0.05) and cultured at 30° C. and 150 rpm (main culture). The culture solutions were collected every 24 hours after the start of the main culture, and β-glucosidase activities of the cells were measured as follows:

(1) wash the cells twice with distilled water;
(2) prepare 500 μL of reaction mixture (composition: 100 μL of 10 mM pNPG (p-nitrophenyl-β-D-glucopyranoside) (final concentration 2 mM); 50 μL of 500 mM sodium citrate buffer solution (pH 5.0) (final concentration 50 mM); 250 μL of distilled water; and 100 μL of yeast cell suspension) (final cell concentration 1 to 10 g wet cells/L)), and allow it to be at 500 rpm and 30° C. for 10 minutes for the reaction;
(3) after the end of the reaction, stop the reaction by adding 500 μL of 3M $Na_2CO_3$; and
(4) centrifuge the mixture at 10,000 g for 5 minutes, and then measure the absorbance at 400 nm, $ABS_{400}$, of the supernatant. One unit of enzyme activity was defined as the amount of enzymes required to liberate 1 μmol of pNP (p-nitrophenol) per minute.

The result is shown in FIG. 1. Symbols in FIG. 1 are as follows: white circles, Gap-Agα1 recombinant strain (Gap-Agα1 type); white diamonds, Gap-Sed1 recombinant strain (Gap-Sed1 type); white triangles, Sed1-Agα1 recombinant strain (Sed1-Agα1 type); and white squares, Sed1-Sed1 recombinant strain (Sed1-Sed1 type). As shown in FIG. 1, it was seen that the Sed1-Sed1 recombinant strain exhibited a BGL activity remarkably higher than that of any of the Gap-Agα1 recombinant strain, the Gap-Sed1 recombinant strain, and the Sed1-Agα1 recombinant strain. In this manner, it is seen that when the promoter and the anchor of Sed1 (SED1) are used in combination, synergistic effects are obtained, and BGL activities are significantly improved compared with the case of using only one of them.

Example 4: Examination for Endoglucanase Activity

The Gap-Agα1 recombinant strain, Gap-Sed1 recombinant strain, Sed1-Agα1 recombinant strain, and Sed1-Sed1 recombinant strain for EGII gene were examined for endoglucanase (EG) activity.

Cells were inoculated to 5 mL of SD medium (supplemented with leucine, methionine, and uracil) and cultured at 30° C. and 180 rpm for 18 hours (pre-culture), and then were inoculated to 50 mL of 1×YPD medium (initial $OD_{600}$=0.05) and cultured at 30° C. and 150 rpm (main culture). The culture solutions were collected 48 hours after the start of the main culture, and endoglucanase activities of the cells were measured as follows:

(1) wash the cells twice with distilled water;
(2) prepare 2500 μL of reaction mixture (composition: one tablet of Cellazyme C (manufactured by Megazyme); 250 μL of 500 mM sodium citrate buffer solution (pH 5.0) (final concentration 50 mM); 2000 μL of distilled water; and 250 μL of yeast cell suspension (final cell concentration 10 g wet cells/L)), and allow it to stand at 38° C. for 4 hours for the reaction;
(3) after the end of the reaction, centrifuge the mixture at 10,000 g for 5 minutes, and then measure the absorbance at 590 nm, $ABS_{590}$, of the supernatant.

Figure 2:
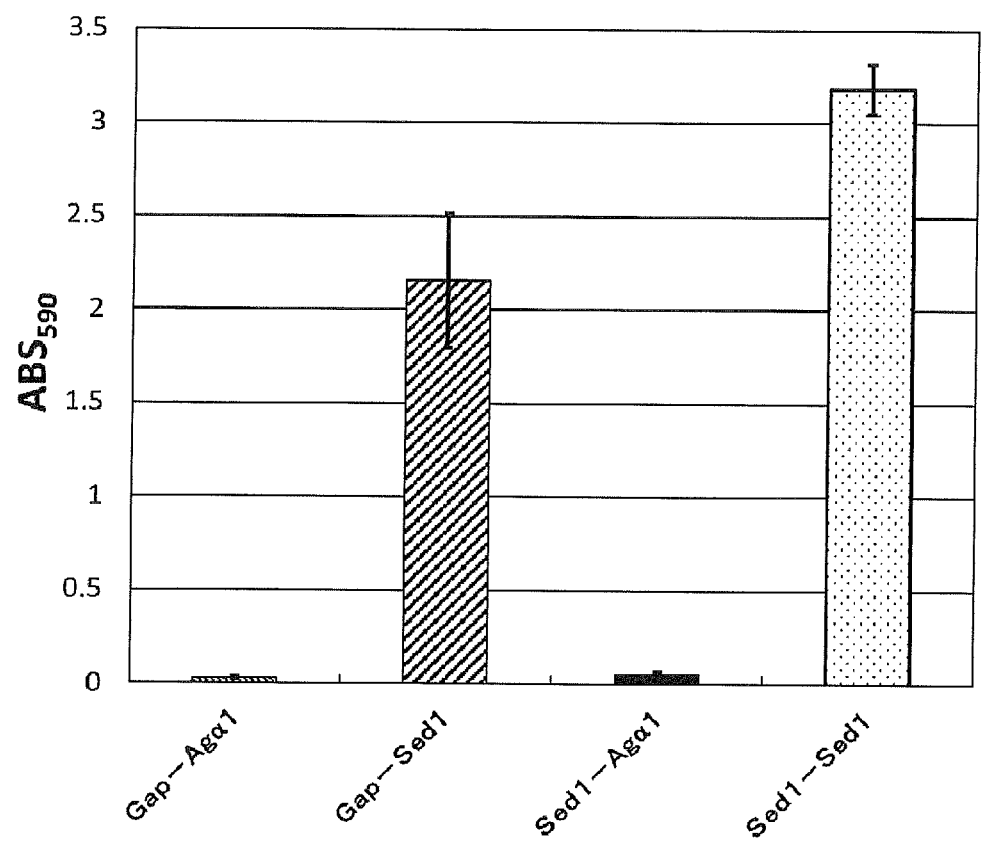
FIG. 2 is a graph showing an endoglucanase activity after culture for 48 hours for the Gap-Agα1 recombinant strain, Gap-Sed1 recombinant strain, Sed1-Agα1 recombinant strain, and Sed1-Sed1 recombinant strain for EGII gene.

The result is shown in FIG. 2. In FIG. 2, the horizontal axis indicates the results of the Gap-Agα1 recombinant strain (Gap-Agα1), the Gap-Sed1 recombinant strain (Gap- Sed1), the Sed1-Agα1 recombinant strain (Sed1-Agα1), and the Sed1-Sed1 recombinant strain (Sed1-Sed1) sequentially from the left, and the vertical axis indicates the light absorbance at 590 nm. As shown in FIG. 2, it was seen that the Sed1-Sed1 recombinant strain exhibited an EG activity remarkably higher than that of any of the Gap-Agα1 recombinant strain, the Gap-Sed1 recombinant strain, and the Sed1-Agα1 recombinant strain. In this manner, it is seen that, also in the case of EG, when the promoter and the anchor of Sed1 (SED1) are used in combination, synergistic effects are obtained, and activities are significantly improved compared with the case of using only one of them.

Example 5: Examination for β-Glucosidase Activity, 2

The Sed1-Sed1 recombinant strain, Gap-Agα1 recombinant strain, and Cwp2-Cwp2 recombinant strain for BGL1 gene were examined for β-glucosidase (BGL) activity, as in Example 3.

Figure 3:
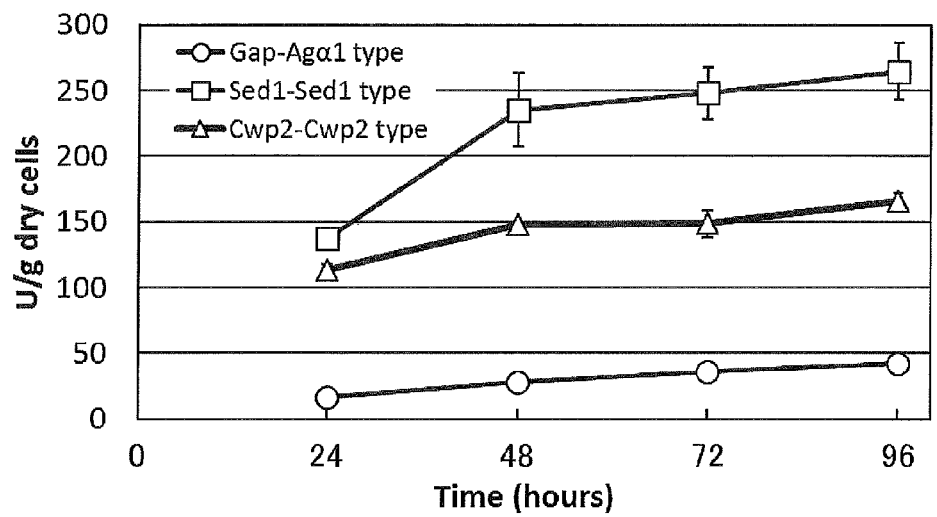
FIG. 3 is a graph showing the time course of a β-glucosidase activity during culture for the Gap-Agα1 recombinant strain, Sed1-Sed1 recombinant strain, and Cwp2-Cwp2 recombinant strain for BGL1 gene.

The result is shown in FIG. 3. Symbols in FIG. 3 are as follows: white circles, Gap-Agα1 recombinant strain (Gap-Agα1 type); white squares, Sed1-Sed1 recombinant strain (Sed1-Sed1 type); and white triangles, Cwp2-Cwp2 recombinant strain (Cwp2-Cwp2 type). As shown in FIG. 3, it was seen that the Sed1-Sed1 recombinant strain exhibited a BGL activity remarkably higher than that of the Gap-Agα1 recombinant strain, and, furthermore, the Cwp2-Cwp2 recombinant strain also exhibited a remarkably increased BGL activity. In this manner, when an anchor and a promoter were derived from the same gene, the activity improving effect obtained by use in combination was not limited to the case of using a combination of those derived from Sed1, and was also seen in the case of using a combination of those derived from other cell surface-localized proteins such as Cwp2 (CWP2).

Example 6: Examination for Hydrolysis of Hydrothermally Processed Rice Straw

The EGII-CBHII gene co-expression type Sed1-Sed1 recombinant strain, EGII-CBHII gene co-expression type Gap-Agα1 recombinant strain, and an empty vector-introduced strain were examined for effect on hydrolysis of hydrothermally processed rice straw.

Cells were inoculated to 10 mL of SD medium (supplemented with methionine and uracil) and cultured at 30° C. and 180 rpm for 18 hours (pre-culture), and then were inoculated to 500 mL of 1×YPD medium (initial $OD_{600}$=0.05) and subjected to stationary culture at 30° C. (main culture). The culture solutions were collected 48 hours after the start of the main culture, and the cells were washed twice with distilled water and used for hydrolysis treatment.

Rice straw was treated with water at 130 to 300° C. and about 10 MPa, and a solid content was collected therefrom and used as hydrothermally processed rice straw.

The hydrolysis treatment was performed under the following conditions:

| | |
|---|---|
| Hydrothermally processed rice straw | 100 g dry weight/L |
| Yeast extract | 10 g/L |
| Peptone | 20 g/L |
| Sodium citrate buffer solution | 50 mM (pH 5.0) |
| Yeast cells | 100 g wet cell weight/L |
| Total | 10 mL |

These were placed in a rotary fermenter, and were incubated at 38° C. and 35 rpm for 96 hours, without adding a commercially available exogenous enzyme.

With the empty vector-introduced strain (no cell surface display), no change was seen in the hydrothermally processed rice straw even after 96 hours. With the EGII-CBHII gene co-expression type Gap-Aged recombinant strain, an increase in the fluidity due to hydrolysis was gradually seen after 48 hours and thereafter. With the EGII-CBHII gene co-expression type Sed1-Sed1 recombinant strain, a significant increase in the fluidity was seen in 15 hours. With such a Sed1-Sed1 recombinant strain, hydrothermally processed rice straw was hydrolyzed to significantly increase the fluidity.

Example 7: Examination for β-Glucosidase Activity, 3

The Sed1-Sed1 recombinant strain, Cwp2-Cwp2 recombinant strain, and Sed1-Cwp2 recombinant strain for BGL1 gene were examined for β-glucosidase (BGL) activity, as in Example 3.

Figure 4:
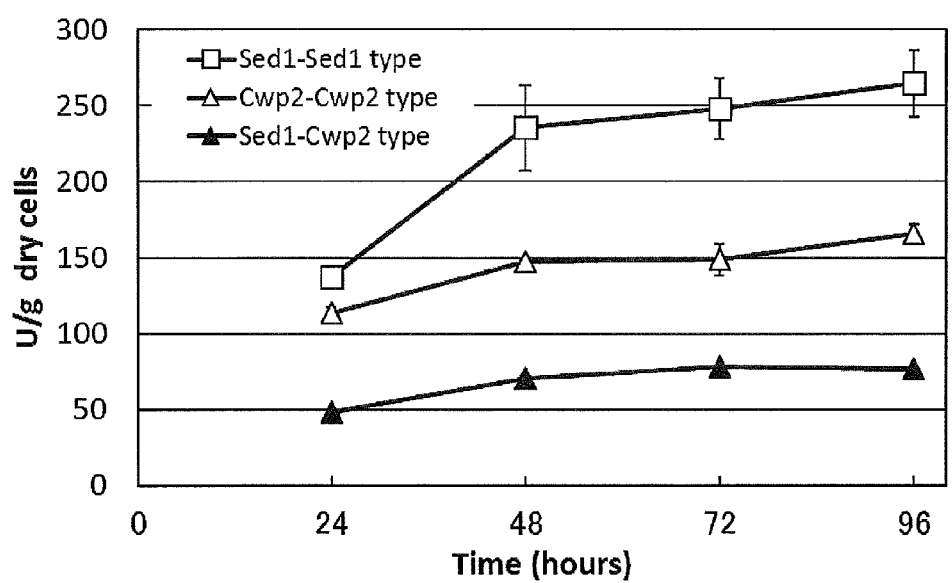
FIG. 4 is a graph showing the time course of a β-glucosidase activity during culture for the Sed1-Sed1 recombinant strain, Cwp2-Cwp2 recombinant strain, and Sed1-Cwp2 recombinant strain for BGL1 gene.

The result is shown in FIG. 4. Symbols in FIG. 4 are as follows: white squares, Sed1-Sed1 recombinant strain (Sed1-Sed1 type); white triangles, Cwp2-Cwp2 recombinant strain (Cwp2-Cwp2 type); and black triangles, Sed1-Cwp2 recombinant strain (Sed1-Cwp2 type). As shown in FIG. 4, it was seen that the Sed1-Cwp2 recombinant strain did not exhibit an increase in the activity as much as that of the Sed1-Sed1 recombinant strain and the Cwp2-Cwp2 recombinant strain, but exhibited an activity increased compared with that of the Gap-Agα1 recombinant strain.

Example 8: Examination for Cell-Surface β-Glucosidase Activity in SED1 Gene Disrupted Strain In this example, the β-glucosidase-displaying yeasts prepared from BY4741 strain and SED1 gene disrupted strain thereof (BY4741 SED1Δ strain) using the coding region and promoter of the gene Sed1 were examined for β-glucosidase (BGL) activity.

The BY4741 strain and the BY4741 SED1Δ strain were transformed with a plasmid pISpBG-PG-Sed1 for BGL1 gene, as in Example 2. The BY4741 SED1Δ strain was obtained from Yeast Knockout Collection Parental Strain-BY4741 (Open Biosystems). The obtained recombinant strains, i.e., the Sed1-Sed1 recombinant BY4741 SED1Δ strain and the Sed1-Sed1 recombinant BY4741 strain were examined for β-glucosidase (BGL) activity, as in Example 3.

Figure 5:
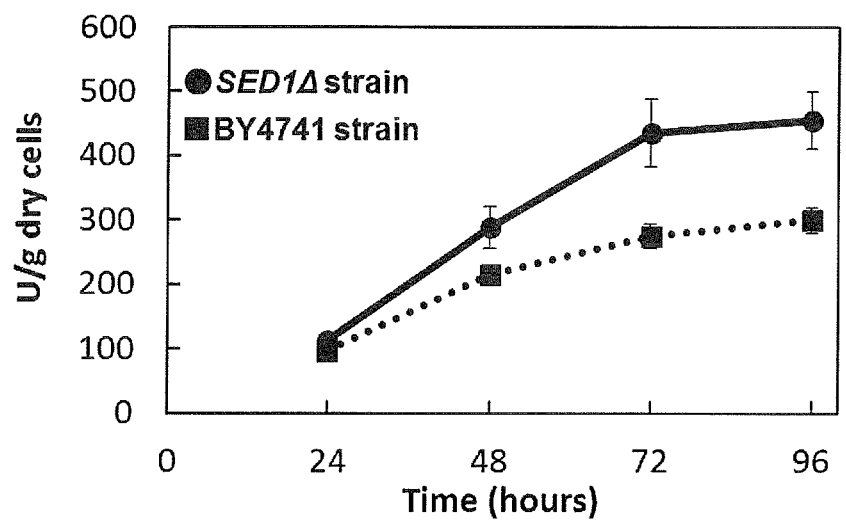
FIG. 5 is a graph showing the time course of a β-glucosidase activity during culture for the Sed1-Sed1 recombinant BY4741 SED1Δ strain and Sed1-Sed1 recombinant BY4741 strain for BGL1 gene.

The result is shown in FIG. 5. Symbols in FIG. 5 are as follows: black circles, Sed1-Sed1 recombinant BY4741 SED1Δ strain (SED1Δ strain); and black squares, Sed1-Sed1 recombinant BY4741 strain (BY4741 strain). As shown in FIG. 5, the Sed1-Sed1 recombinant BY4741 SED1Δ strain exhibited a maximum cell-surface BGL activity increased compared with that of the Sed1-Sed1 recombinant BY4741 strain, and exhibited a remarkably increased BGL activity especially after culture for 72 hours and thereafter.

Example 9: Examination for Cell-Surface β-Glucosidase Activity in SSD1 Gene Disrupted Strain In this example, the β-glucosidase-displaying yeasts prepared from BY4741 strain and SSD1 gene disrupted strain thereof (BY4741 SSD1Δ strain) using the coding region and promoter of the gene Sed1 were examined for β-glucosidase (BGL) activity.

The BY4741 strain and the BY4741 SSD1Δ strain were transformed with a plasmid pISpBG-PG-Sed1 for BGL1 gene, as in Example 2. The BY4741 SSD1Δ strain was obtained from Yeast Knockout Collection Parental Strain-BY4741 (Open Biosystems). The obtained recombinant strains, i.e., the Sed1-Sed1 recombinant BY4741 SSD1Δ strain and the Sed1-Sed1 recombinant BY4741 strain were examined for β-glucosidase (BGL) activity, as in Example 3.

Figure 6:
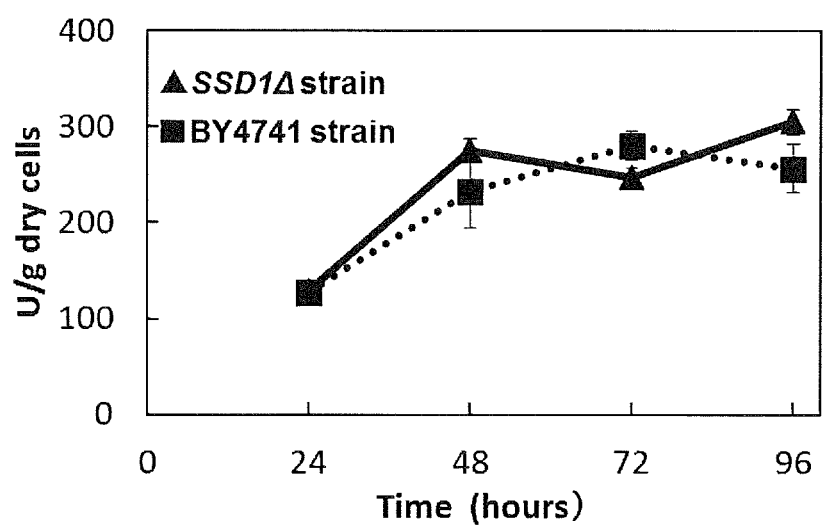
FIG. 6 is a graph showing the time course of a β-glucosidase activity during culture for the Sed1-Sed1 recombinant BY4741 SSD1Δ strain and Sed1-Sed1 recombinant BY4741 strain for BGL1 gene.

The result is shown in FIG. 6. Symbols in FIG. 6 are as follows: black triangles, Sed1-Sed1 recombinant BY4741 SSD1Δ strain (SSD1Δ strain); and black squares, Sed1-Sed1 recombinant BY4741 strain (BY4741 strain). As shown in FIG. 6, the Sed1-Sed1 recombinant BY4741 SSD1Δ strain did not exhibit a significant increase in the maximum cell-surface BGL activity compared with that of the Sed1-Sed1 recombinant BY4741 strain, but exhibited a BGL activity somewhat increased after culture for 48 hours. Furthermore, the total cell amount of the Sed1-Sed1 recombinant BY4741 SSD10 strain increased to 1.16 times after culture for 48 hours and to 1.26 times after 96 hours compared with the Sed1-Sed1 recombinant BY4741 strain, and thus, the total BGL activity exhibited by the cells obtained by the culture was significantly increased.

Example 10: Examination for Cell-Surface β-Glucosidase Activity in Double-Disrupted Strain In this example, the β-glucosidase-displaying yeasts prepared from BY4741 strain having disrupted SED1 and SSD1 genes (double-disrupted strain), as well as BY4741 strain, BY4741 SED10 strain, and BY4741 SSD1Δ strain using the coding region and promoter of the gene Sed1 were examined for were examined for β-glucosidase (BGL) activity.

The double-disrupted strain of the Sed1-Sed1 recombinant BY4741 strain was prepared as follows. About 1.1 kb of DNA fragment having a Zeocin-resistant gene and 30b sequences homologous with regions upstream and downstream of the SED1 gene respectively arranged at both termini was prepared by PCR using a plasmid pTEF1/Zeo (obtained from Invitrogen) as a template with a primer pair SED1d-zeo-F1 (SEQ. ID. No. 40) and SED1d-zeo-R1 (SEQ. ID. No. 41). Furthermore, about 1.2 kb of DNA fragment having a Zeocin-resistant gene and 80b sequences homologous with regions upstream and downstream of the SED1 gene respectively arranged at both termini was prepared through amplification again by PCR using the above-described fragment as a template with a primer pair SED1d-zeo-F2 (SEQ. ID. No. 42) and SED1d-zeo-R2 (SEQ. ID. No. 43). This DNA fragment was provided with the Sed1-Sed1 recombinant SSD1Δ strain obtained in Example 9 to transform the strain by lithium acetate treatment procedure, after which a Zeocin-resistant strain was selected so that a SED1 and SSD1 double-disrupted strain was obtained. The obtained recombinant strain was referred to as a Sed1-Sed1 recombinant BY4741 SED1ΔSSD1Δ strain.

The Sed1-Sed1 recombinant BY4741 strain, Sed1-Sed1 recombinant BY4741 SED1Δ strain, Sed1-Sed1 recombinant BY4741 SSD1Δ strain, and Sed1-Sed1 recombinant BY4741 SED1ΔSSD1Δ strain were examined for β-glucosidase (BGL) activity, as in Example 3.

Figure 7:
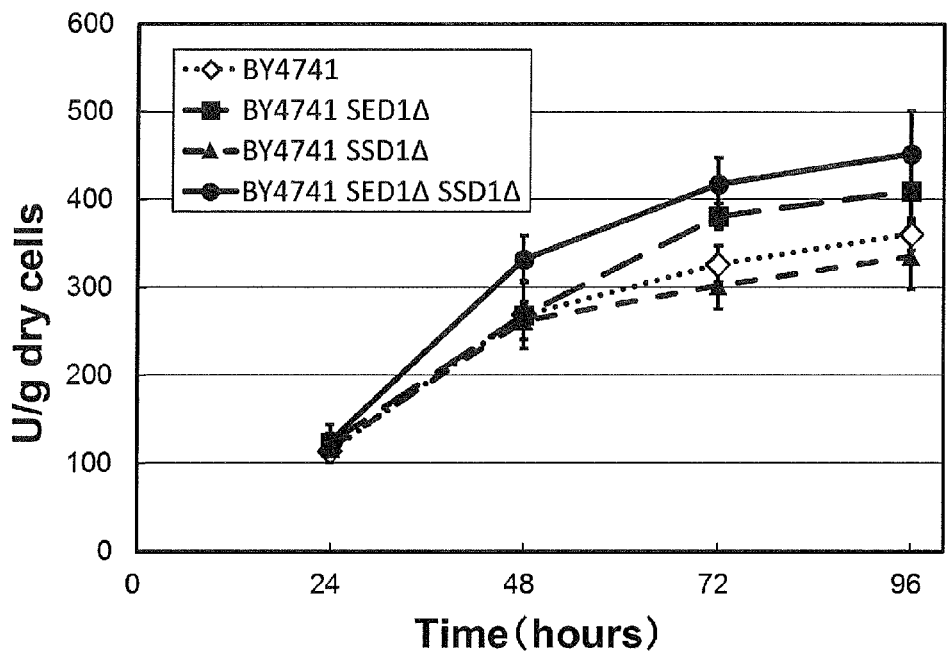
FIG. 7 is a graph showing the time course of a β-glucosidase activity during culture for the Sed1-Sed1 recombinant BY4741 strain, Sed1-Sed1 recombinant BY4741 SED1Δ strain, Sed1-Sed1 recombinant BY4741 SSD1Δ strain, and Sed1-Sed1 recombinant BY4741 SED1ΔSSD1Δ for BGL1 gene.

The result is shown in FIG. 7. Symbols in FIG. 7 are as follows: white diamonds, Sed1-Sed1 recombinant BY4741 strain (BY4741); black squares, Sed1-Sed1 recombinant BY4741 SED1Δ strain (BY4741 SED1Δ); black triangles, Sed1-Sed1 recombinant BY4741 SSD1Δ strain (BY4741 SSD1Δ); and black circles, Sed1-Sed1 recombinant BY4741 SED1ΔSSD1Δ strain (BY4741 SED1ΔSSD1Δ). As shown in FIG. 7, it was found that a maximum value and an increase rate of the cell-surface BGL activity for the double-disrupted strain as a host (Sed1-Sed1 recombinant BY4741 SED1ΔSSD1Δ strain) expressing the SED1 type cell surface display cassette were higher than those for the SED1 single disrupted strain as a host (Sed1-Sed1 recombinant BY4741 SED1Δ strain). Furthermore, the total cell amount of the Sed1-Sed1 recombinant BY4741 SED1ΔSSD1Δ strain increased to 1.10 times after 48 hours and to 1.20 times after 96 hours compared with the Sed1-Sed1 recombinant BY4741 strain, and the effects were seen substantially similar to those in the case where the SSD1 single disrupted strain was used as a host (Sed1-Sed1 recombinant BY4741 SED1Δ strain).

Example 11: Examination for Ethanol Productivity

The Sed1-Sed1 recombinant strain and Gap-Agα1 recombinant strain for EGII gene were examined for ethanol productivity.

In this example, two types of EGII-displaying strains expressing the EGII gene on the cell surface, that is, EGII-displaying Sed1-Sed1 recombinant strain and EGII-displaying Gap-Agα1 recombinant strain, and an empty vector-introduced strain (no cell surface display) were used. This examination was conducted as in the procedure in Example 6, except that a culture solution having the following composition was used for fermentation culture:

| | |
|---|---|
| Hydrothermally processed rice straw | 100 g dry weight/L |
| Yeast extract | 10 g/L |
| Peptone | 20 g/L |
| Sodium citrate buffer solution | 50 mM (pH 5.0) |
| Yeast cells | 100 g wet cell weight/L |
| Exogenous enzyme (Ctec2: manufactured by Novozymes) | 1 FPU/10 mL |
| Total | 10 mL |

Figure 8:
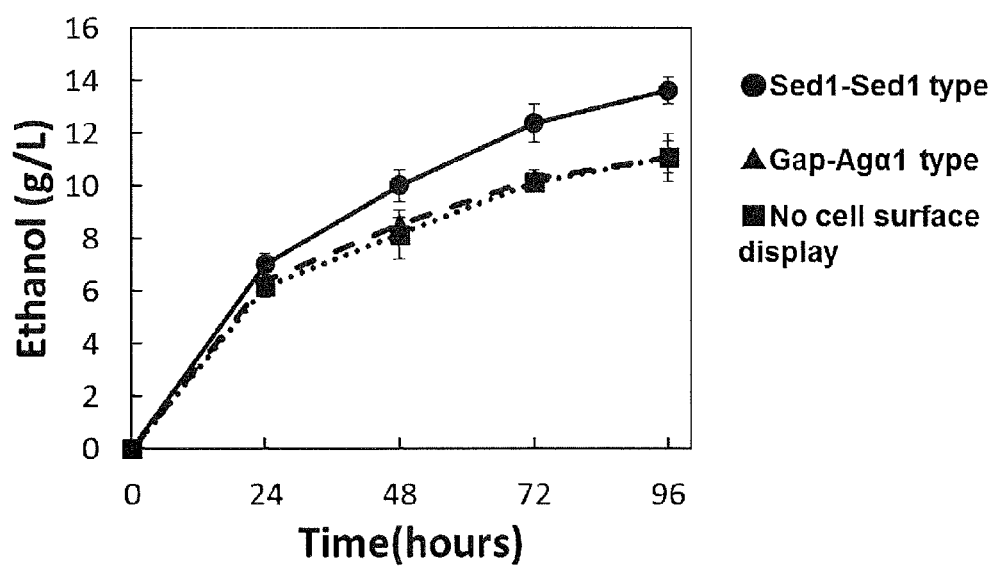
FIG. 8 is a graph showing the time course of the amount of ethanol produced during fermentation culture for the Sed1-Sed1 recombinant strain and Gap-Agα1 recombinant strain for EGII gene, and an empty vector-introduced strain (no cell surface display).

The result is shown in FIG. 8. Symbols in FIG. 8 are as follows; black circles, EGII-displaying Sed1-Sed1 recombinant strain (Sed1-Sed1 type); black triangles, EGII-displaying Gap-Agα1 recombinant strain (Gap-Agα1 type); and black squares, empty vector-introduced strain (no cell surface display). As shown in FIG. 8, the EGII-displaying Gap-Agα1 recombinant strain was not so much different from the empty vector-introduced strain of no cell surface display in terms of the rate and yield of the ethanol production in simultaneous saccharification and fermentation using hydrothermally processed rice straw, whereas the Sed1-Sed1 recombinant strain remarkably increased in the rate and yield.

Example 12: Preparation of Vector for Amylase Cell Surface Display

The preparation of *Rhizopus oryzae*-derived glucoamylase gene, and *Streptococcus bovis*-derived α-amylase gene were carried out as set forth below.

A glucoamylase gene fragment was prepared through amplification by PCR using pδU-PGGluRAG (a vector for cell surface expression of glucoamylase having a 3' half region of α-agglutinin gene: Non-Patent Document 9) as a template with a primer pair pIBGvsp-CBA-F (SEQ. ID. No. 11) and GA-CBA-R (SEQ. ID. No. 44).

A gene fragment containing a fragment encoding the secretion signal peptide of yeast *Saccharomyces cerevisiae* a factor and *Streptococcus bovis*-derived α-amylase gene was prepared through amplification by PCR using pUPGS-BAAG (a vector for cell surface expression of α-amylase having a 3' half region of α-agglutinin gene: Non-Patent Document 10) as a template with a primer pair AA-CBA-F (SEQ. ID. No. 45) and AA-CBA-R (SEQ. ID. No. 46) for α-amylase.

A gene fragment containing the glucoamylase gene, or a gene fragment containing the α factor secretion signal peptide coding fragment and the α-amylase gene was ligated, by one-step isothermal assembly, to a fragment amplified respectively using a vector plasmid pINCCB-Sed1 or pISpBG-PG-Sed1 as a template with a primer pair SED1aga-CBA-F (SEQ. ID. No. 47) and SED1p-CBA-R (SEQ. ID. No. 10), or SED1aaa-CBA-F (SEQ. ID. No. 48) and SED1p-CBA-R2 (SEQ. ID. No. 49). The obtained plasmids were named pINCGA-Sed1 and pISpAA-Sed1.

Example 13: Preparation of Amylase-Displaying Yeast

A plasmid (pISpAA-Sed1) for α-amylase gene was treated with NdeI, and was provided with yeast *Saccharomyces cerevisiae* BY4741 strain (MATα his3 leu2 met15 ura3 strain) to transform the strain by lithium acetate treatment procedure. This recombinant strain is referred to as a Sed1-Sed1 recombinant strain for α-amylase gene.

A plasmid (pINCGA-Sed1) for glucoamylase gene was treated with NdeI, and was provided with the Sed1-Sed1 recombinant strain (MATα leu2 met15 ura3 strain) for α-amylase gene to transform the strain by lithium acetate treatment procedure. This recombinant strain is referred to as an α-amylase-glucoamylase gene co-expression type Sed1-Sed1 recombinant strain.

Example 14: Examination for α-Amylase and Glucoamylase Activities

The α-amylase-glucoamylase gene co-expression type Sed1-Sed1 recombinant strain was examined for α-amylase and glucoamylase activities.

Cells were inoculated to 5 mL of SD medium (supplemented with methionine and uracil) and cultured at 30° C. and 180 rpm for 18 hours (pre-culture), and then were inoculated to 50 mL of 1×YPD medium (initial $OD_{600}$=0.05) and cultured at 30° C. and 150 rpm (main culture). The culture solution was collected every 24 hours after the start of the main culture, and the cells were washed twice with distilled water. The α-amylase and glucoamylase activities of the cells were measured respectively using an α-amylase assay kit (manufactured by Kikkoman Corporation) and a saccharification assay kit (manufactured by Kikkoman Corporation), at pH 5.0 and 37° C.

Figure 9:
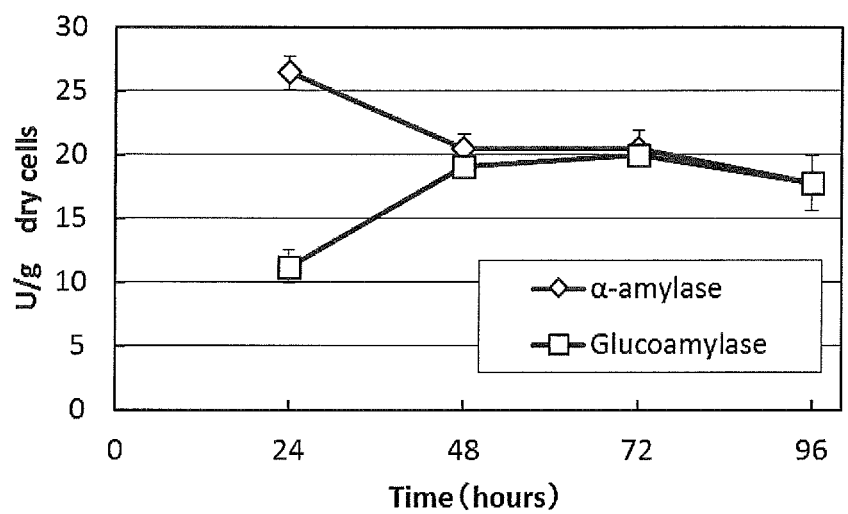
FIG. 9 is a graph showing the time course of α-amylase and glucoamylase activities during culture for the α-amylase-glucoamylase gene co-expression type Sed1-Sed1 recombinant strain.

The result is shown in FIG. 9. In FIG. 9, white diamonds indicate the measurement result of α-amylase activity, and white squares indicate the measurement result of glucoamylase activity. As shown in FIG. 9, it was seen that the α-amylase-glucoamylase gene co-expression type Sed1-Sed1 recombinant strain exhibit a high α-amylase activity and a high glucoamylase activity together. In this manner, starch-degrading enzyme (α-amylase and glucoamylase) were demonstrated to be displayed on the cell surface, same as cellulose-degrading enzymes (endoglucanase, cellobiohydrolase, and β-glucosidase).

Example 15: Examination for Simultaneous Saccharification and Fermentation of Starch The α-amylase-glucoamylase gene co-expression type Sed1-Sed1 recombinant strain was examined for the productivity of ethanol from raw starch.

Cells were inoculated to 10 mL of SD medium (supplemented with methionine and uracil) and cultured at 30° C. and 180 rpm for 18 hours (pre-culture), and then were inoculated to 500 mL of 1×YPD medium (initial $OD_{600}$=0.05) and cultured at 30° C. and 150 rpm (main culture). The culture solution was collected 72 hours after the start of the main culture, and the cells were washed twice with distilled water and used for simultaneous saccharification and fermentation.

Corn-derived starch (manufactured by Wako Pure Chemical Industries, Ltd.) was used as raw starch.

The hydrolysis treatment was performed under the following conditions:

| | |
|---|---|
| Raw starch | 200 g dry weight/L |
| Yeast extract | 10 g/L |
| Peptone | 20 g/L |
| Yeast cells | 50 g wet cell weight/L |
| Total | 5 mL |

These were placed in a rotary fermenter, and were incubated at 30° C. and 35 rpm for 120 hours, without adding a commercially available exogenous enzyme.

Figure 10:
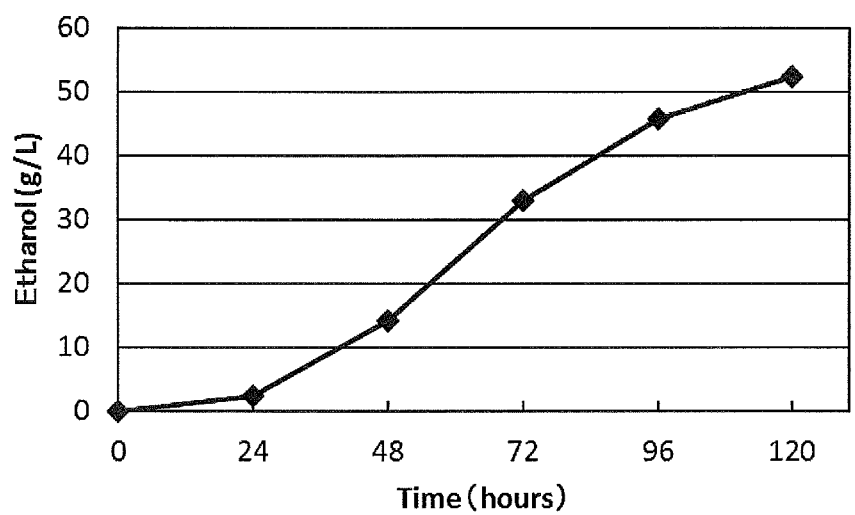
FIG. 10 is a graph showing the time course of the amount of ethanol produced from raw starch by the α-amylase-glucoamylase gene co-expression type Sed1-Sed1 recombinant strain.

The result is shown in FIG. 10. With the α-amylase-glucoamylase gene co-expression type Sed1-Sed1 recombinant strain, raw starch was hydrolyzed and directly converted to ethanol by the yeast cells alone without adding a commercially available exogenous enzyme.

INDUSTRIAL APPLICABILITY

Provided is a polynucleotide for cell surface expression that allows for the production of a yeast displaying a protein such as an enzyme on the cell surface with a high activity. A yeast into which this polynucleotide has been introduced can express a protein on the cell surface with a high activity. For example, if the protein is a cellulose-degrading enzyme, it is applicable to produce biofuels (ethanol, butanol, isoprenoid, etc.) and chemical polymer materials (isopropanol, amino acid, organic acid, quinones, etc.) from cellulosic biomass. Effective use of biomass not only reduces the environmental load but also suppresses $CO_2$ emissions due to use of fossil resources.

The invention claimed is:

1. A polynucleotide for cell surface expression, comprising various heterologous elements: a) an SED1 promoter of SEQ ID NO: 5, b) a sequence encoding a secretion signal peptide of *Rhizopus oryzae*-derived glucoamylase or *Saccharomyces cerevisiae* α factor, c) a sequence encoding an intended protein, and d) a sequence encoding a cell surface-localized protein SED1 of SEQ ID NO: 2 or a cell membrane-binding domain thereof including positions 110 to 338 of SEQ ID NO: 2, said intended protein being a protein selected from the group consisting of enzyme, antibody, ligand and fluorescent protein.

2. An expression vector, comprising the polynucleotide for cell surface expression of claim 1.

3. A recombinant yeast into which the polynucleotide for cell surface expression of claim 1 has been introduced.

4. The recombinant yeast of claim 3, obtained from a host yeast in which at least one selected from the group consisting of SED1 and SSD1 is deficient.

5. The recombinant yeast of claim 4, obtained from a host yeast in which SED1 and SSD1 are deficient.

6. The recombinant yeast of claim 3, displaying at least one enzyme selected from the group consisting of cellulose-degrading enzymes and starch-degrading enzymes on the cell surface.

7. A method for producing ethanol, comprising:

performing fermentation culture of the recombinant yeast of claim 6.

8. A recombinant yeast into which the expression vector of claim 2 has been introduced.

9. The recombinant yeast of claim 8, obtained from a host yeast in which at least one selected from the group consisting of SED1 and SSD1 is deficient.

10. The recombinant yeast of claim 9, obtained from a host yeast in which SED1 and SSD1 are deficient.

11. The recombinant yeast of claim 8, displaying at least one enzyme selected from the group consisting of cellulose-degrading enzymes and starch-degrading enzymes on the cell surface.

* * * * *